US008557234B1

(12) United States Patent
Davis et al.

(10) Patent No.: US 8,557,234 B1
(45) Date of Patent: Oct. 15, 2013

(54) METHODS OF CONTROLLING PIT FOAM

(75) Inventors: Mari Ellen Davis, Waukesha, WI (US); Terry D. Parrott, El Reno, OK (US); Joshua M. Rehberger, Milwaukee, WI (US); Thomas G. Rehberger, Wauwatosa, WI (US); Ardean Veldkamp, Oostburg, WI (US); Daniel Petri, Waukesha, WI (US)

(73) Assignee: DuPont Nutrition Biosciences ApS, Copenhagen (DK)

( * ) Notice: Subject to any disclaimer, the term of this patent is extended or adjusted under 35 U.S.C. 154(b) by 155 days.

(21) Appl. No.: 13/110,529

(22) Filed: May 18, 2011

Related U.S. Application Data

(66) Substitute for application No. 61/345,925, filed on May 18, 2010.

(51) Int. Cl.
*A01N 63/00* (2006.01)

(52) U.S. Cl.
USPC .................................. 424/93.462; 435/252.5

(58) Field of Classification Search
None
See application file for complete search history.

(56) References Cited

U.S. PATENT DOCUMENTS

| | | | |
|---|---|---|---|
| 2,906,622 | A | 9/1959 | Lewis |
| 2,942,977 | A | 6/1960 | Lewis |
| 4,820,531 | A | 4/1989 | Tomes |
| 4,919,936 | A | 4/1990 | Iwanami |
| 5,478,557 | A | 12/1995 | Nisbet |
| 5,482,723 | A | 1/1996 | Susaki |
| 5,507,250 | A | 4/1996 | Reddy |
| 5,540,924 | A | 7/1996 | Onishi |
| 5,703,040 | A | 12/1997 | Landolo |
| 5,718,894 | A | 2/1998 | Mann |
| 5,830,993 | A | 11/1998 | Biecha |
| 5,840,318 | A | 11/1998 | Marshall |
| 5,879,719 | A | 3/1999 | Valentine |
| 5,945,333 | A | 8/1999 | Rehberger |
| 5,964,187 | A | 10/1999 | Willis |
| 5,965,128 | A | 10/1999 | Doyle |
| 6,008,195 | A | 12/1999 | Selsted |
| 6,156,355 | A | 12/2000 | Shields, Jr. |
| 6,207,411 | B1 | 3/2001 | Ross |
| 6,221,650 | B1 | 4/2001 | Rehberger |
| 6,346,422 | B1 | 2/2002 | Butty |
| 6,410,016 | B2 | 6/2002 | Maruta |
| 7,247,299 | B2 | 7/2007 | Lin et al. |
| 7,354,757 | B2 | 4/2008 | Rehberger et al. |
| 7,384,628 | B2 | 6/2008 | Rehberger et al. |
| 8,221,742 | B2 | 7/2012 | Rehberger et al. |
| 8,404,227 | B2 | 3/2013 | Bellot et al. |
| 8,420,074 | B2 | 4/2013 | Rehberger et al. |
| 8,444,966 | B2 | 5/2013 | Rehberger et al. |
| 2002/0018770 | A1 | 2/2002 | Maruta |
| 2003/0099624 | A1 | 5/2003 | Porubcan |
| 2004/0170617 | A1 | 9/2004 | Finegold |
| 2005/0255092 | A1 | 11/2005 | Rehberger |
| 2007/0202088 | A1 | 8/2007 | Baltzley et al. |
| 2009/0275109 | A1 | 11/2009 | Bellot et al. |
| 2009/0280090 | A1 | 11/2009 | Rehberger |

FOREIGN PATENT DOCUMENTS

WO 2004104175 5/2004

OTHER PUBLICATIONS

Davis et al., J. Anim. Sci., 2008, 86:1459-1467.*
http://www.alken-murray.com/EZ4pib.htm, accessed Jan. 15, 2013.*
Teo et al., "Applied & Environmental Microbiology," (Aug. 2005) vol. 71, 8:4185-4190.
Timmerman, H. M. et al, "Health and growth of veal calves fed milk replacers with or without probiotics," J. Dairy Sci. (2005) 88:2154-2165.
Torrallardona, D. et al, "Effect of fishmeal replacement with spray-dried plasma and colistin on intestinal structure, intestinal microbiology, and performance of weanling pigs challenged with *Escherichia coli* K99," J. Anim. Sci. (2003) 81:1220-1226.
Van Dijk, A. et al, "Growth performance of weanling pigs fed spray-dried animal plasma: a review," Livestock Production Science (2001a) 68:263-274.
Van Dijk, A. et al, "Growth performance and health status in weanling piglets fed spray-dried porcine plasmas under typical Northern European conditions," J. Anim. Physiol. Anim. Nutr. (Berl). (2002b) 86:17-25.
Vance, H. N., "A survey of the alimentary tract of cattle for *Clostridium perfringens*," Can. J. Comp. Med. Vet. Sci. (1967) 31:260-264.
"Watt Feed E-News Feb. 8, 2005" 'Online! Feb. 8, 2005, pp. 1-6, XP002342563, retrieved from the Internet: URL:http://www.wattnet.com/Newsletters/feed/htm/FEBFEED05.htm> [source: PCT/US05/017141 ISR].
Wattiau, P. et al, "A PCR test to identify *Bacillus subtilis* and closely related species and its application to the monitoring of wastewater biotreatment," Appl Microbiol Biotechnol 56:816-819, 2001.
Wattiau et al, Appl. Microbiol Biotechnol 2001, vol. 56, p. 816-819.
Wiard, T et al, "The effect of a biological litter treatment on Salmonella prevalence in turkey breeder flock litter," Poultry Science 80:127 (Suppl. 1):1-4, 2001.
Casey, P. G. et al, "A five-strain probiotic combination reduces pathogen shedding and alleviates disease signs in pigs challenged with *Salmonella enterica* serovar Typhimurium," Appl. Environ. Microbiol, (2007) 73:1858-1863.
Wiard, T et al, Application of plating enumerations and denaturing gradient gel electrophoresis to study turkey poult gastrointestinal tract bacterial diversity, (4 pgs) presented at the Poultry Science Assoc meeting, Madison, WI 2003.

(Continued)

*Primary Examiner* — Irene Marx
(74) *Attorney, Agent, or Firm* — Whyte Hirschboeck Dudek S.C.

(57) ABSTRACT

A method of controlling foam in a manure pit. In the method, one or more *Bacillus* strain(s) is administered in an effective amount to animals whose manure is stored in the manure pit. Also provided is a method of controlling foam in a manure storage unit. In the method, one or more *Bacillus* strain(s) is administered in an effective amount to the manure storage unit.

6 Claims, 3 Drawing Sheets

(56) References Cited

OTHER PUBLICATIONS

Wiard, T et al, "Application of plating enumerations and denaturing gradient gel electrophoresis to study turkey poult gastrointestinal tract bacterial diversity," Poster #244 and its abstract, presented at the Poultry Science Assoc meeting, Madison, WI 2003.

Williams, J. G. et al, "DNA polymorphisms amplified by arbitrary primers are useful as genetic markers," Nucleic Acids Res. (1990) 18:6531-6535.

Willoughby, D H et al, "Periodic recurrence of gangrenous dermatitis associated with *Clostridium speticum* in a broiler chicken operation," J Vet Diagn Invest 8:259-261, 1996.

Wills, "*Escherichia coli* postweaning diarrhea," Vet Clinics N Am, pp. 138-140, 2000.

Wilson, M, "Segregated early weaning," Pig Lett. (1995) 15:17-20.

Wistuba et al, "Influence of fish oil supplementation on growth and immune system characteristics of cattle," J. Anim. Sci. (2005) 83:1097-1101.

Wu, X. Y. et al, "Characterization of mesophilic bacilli in feces of feedlot cattle," J. Appl. Microbiol. (2007) 102:872-879.

Yang, H. et al, "Effect of adding a bacillus based direct fed microbial on performance of nursery pigs fed diets with or without antibiotics," J. Anim. Sci. (2003).

Yang, W., "Effects of direct-fed microbial supplementation on ruminal acidosis, digestibility, and bacterial protein synthesis in continuous culture," Animal Feed Science and Technology, (2004) 114(4): 179-193.

Zhu, X Y, "16S rRNA-based analysis of microbiota from the cecum of broiler chickens," Applied and Environmental Microbiology, 68(1):124-137, Jan. 2002.

Zoetendal, E G et al, Molecular ecological analysis of the gastrointestinal microbiota: a review, J of Nutrition pp. 465-472, 2004.

International Search Report and The Written Opinion of the International Searching Authority, or the Declaration mailed Dec. 9, 2005 for PCT/US2005/017141, filed on May 13, 2005.

International Search Report and The Written Opinion of the International Searching Authority, or the Declaration mailed Dec. 6, 2009 for PCT/US2009/40920, filed on Apr. 17, 2009.

Non-Final Office Action mailed May 13, 2009 for U.S. Appl. No. 11/565,474, filed Nov. 30, 2006.

Notice of Allowance, mailed Apr. 10, 2009 for U.S. Appl. No. 11/129,767, filed May 13, 2005.

Final Office Action mailed Jan. 22, 2009 for U.S. Appl. No. 11/129,767, filed May 13, 2005.

Non-Final Office Action mailed Feb. 5, 2008 for U.S. Appl. No. 11/129,767, filed May 13, 2005.

Bernet, N. and F. Beline. 2009. Challenges and innovations on biological treatment of livestock effluents. Bioresource Technology 100:5431-5436.

Brumm, M. 2009. Brumm Speaks Out blog located at www.mnpork.com/forum/index.php accessed on Oct. 20, 2009.

Davis, M.E., et al., "effect of a Bacillus-based direct-fed microbial feed supplement on growth performance and pen cleaning characteristics of growing-finishing pigs" J. Anim Sci 2008, 86: 1459-1467.

Gonzalez-Fernandez, C. and P. A. Garcia-Encina. 2009. Impact of substrate to inoculum ratio in anaerobic digestion of swine slurry. Biomass and Bioenergy 33:1065-1069.

Hoff, S. J., D. S. Bundy, M. A. Nelson, B. C. Zelle, L. D. Jacobson, A. J. Heber, N. I. Jinqin; Y. Zhang, J. A. Koziel, and D. B. Beasley. 2006. Emissions of ammonia, hydrogen sulfide, and odor before, during, and after slurry removal from a deep-pit swine finisher. Journal of the Air & Waste Management Association 56:581-590.

Moody, L. et al., "Deep Pit Swine Facility Flash Fires and Explosions: Sources, Occurrences, Factors, and Management", Department of Agricultural and Biosystems Engineering Iowa State University, Dec. 21, 2009.

Peu, P., H. Brugere, A. Pourcher, M. Kerouredan, J. Godon, J. Delgenes, and P. Dabert. 2006. Dynamics of a pig slurry microbial community during anaerobic storage and management. Applied and Environmental Microbiology 72:3578-3585.

Rehberger, J., E. Davis, A. Baker, T. Parrott, A. Veldkamp, and T. Rehberger. 2009. A preliminary comparison of bacterial communities of foaming and non-foaming swine manure pits. Journal of Animal Science 87(Suppl. 2):492.

Stein, H. H. And G. C. Shurson. 2009. Board Invited Review: The use and application of distillers dried grains with solubles in swine diets. Journal of Animal Science 87:1292-1303.

Shurson, J. 2009. Analysis of current feeding practices of distiller's grains with soluble in livestock and poultry feed relative to land use credits associated with determining the low carbon fuel standard for ethanol. Accessed at: www.ethanolrfa.org/objects/documents/2288/rfa.analysis_of_current_feeding_practices_of_distiller_final_3-25-09.pdf on Oct. 23, 2009.

Snell-Castro, R., J. Godon, J. Delgenes, and P. Dabert. 2005. Chracterization of the microbial diversity in a pig manure storage pit using small subunit rDNA sequence analysis. FEMS Microbiology Ecology 52:229-242.

Soddell, J. A. And R. J. Seviour. 1990. Microbiology of foaming in activated sludge plants. Journal of Applied Bacteriology 69:145-176.

Zhu, J. 2000. A review of microbiology in swine manure odor control. Agriculture, Ecosystems, and Environment 78: 93-106.

Bitton, G. 1994. Bulking and foaming in activated sludge plants. In Wastewater Microbiology. John Wiley & Sons, Inc., New York: pp. 167-187.

Fu, S. X., M. Johnston, R. W. Fent, D. C. Kendall, J. L. Usry, R. D. Boyd, and G. L. Allee. 2004. Effect of corn distiller's dried grains with soluble (DDGS) on growth, carcass characteristics and fecal volume in growing-finishing pigs. Journal of Animal Science 82 (Suppl. 2):80.

Pagilla, K., K. Craney, and W. Kido. 1997. Causes and effects of foaming in anaerobic sludge digesters. Water Science Technology 36:463-470.

Pagilla, K. R., A. Sood, and H. Kim. 2002. Gordonia (Nocoardia) amarae foaming due to biosurfactant production. Water Science and Technology 46:519-524.

Whitehead, T. R. and M. A. Cotta. 2001. Characterization and comparison of microbial populations in swine faeces and manure storage pits by 16S rDNA gene sequence analyses. Anaerobe 7:181-187.

Wolfe, R. S. 1971. Microbial formation of methane. Adv. Microbiol. Physiol. 6: 107-145.

Abe, F. et al, "Effect of administration of Bifidobacteria and lactic acid bacteria to newborn calves and piglets," J. Dairy Sci. (1995) 78:2838-2846.

Adami, A. et al, "Piglets fed from birth with the probiotic *Bacillus coagulans* as additive: zootechnical and microbiological aspects," Ann Microbiol Enzimol (1997) 47: 139-149.

Allison, M .J. et al, "Grain overload in cattle and sheep: Changes in microbial populations in the cecum and rumen," Amer. J. Vet Res. (1975) 36:181.

Awad, M M et al, "Synergistic effects of alpha-toxin and perfringolysin O in *Clostridium perfringens*-medicated gas gangrene," Infection & Immunity, 69(12):7904-7910, 2001.

Baker, A. et al, "Development of a *Bacillus subtilis* product for a large commercial swine farm to reduce *Clostridium perfringens* and *Clostridium difficile* in neonatal pigs," J. Anim. Sci. (2007) 85(suppl. 1):102.

Baker, G. C. et al, "Review and re-analysis of domain-specific 16S primers," Journal of Microbiological Methods (2003) 55:541-555.

Banach, S et al, "Prevalence, distribution and diversity of pathogenic *E. coli* in commercial turkey poult production," Presented at the Poultry Science Association Annual Meeting, Madison, WI, Jul. 2003.

Banach, S et al, "Prevalence, distribution and diversity of pathogenic *E. coli* in commercial turkey poult production," Poster #337, presented at the Poultry Science Association Annual Meeting, Madison, WI, Jul. 2003.

Barbosa, et al, "Applied and Environmental Microbiology," (Feb. 2005) vol. 71, 2:968-978.

Bembridge et al. "CD45RO expression on bovine T cells: relation to biological function," Immunology, (1995) 86:537-544.

(56) References Cited

OTHER PUBLICATIONS

Bertschinger, H U, "*Escherichia coli* infections," Diseases of Swine 8th Ed., Chap. 32, pp. 431-454, 1999.
Bikker, P. et al, "The influence of diet composition and an antimicrobial growth promoter on the growth response of weaned piglets to spray dried animal plasma." Livestock Prod. Sci. (2004) 86:201-208.
Billington et al., "*Clostridium perfringens* Type E animal enteritis isolates with highly conserved, silent enterotoxin gene sequences," Infect. Immun. (1998) 66(9):4531-4536.
Blood, D C, "Diseases caused by bacteria," Veterinary Medicine, 7th Ed., Bailliere, pp. 637-640, 1989.
Bosi, P. et al, "Effect of different spray dried plasmas on growth, ileal digestibility, nutrient deposition, immunity and health of early-weaned pigs challenged with *E. coli* K88," Asian-Aust. J. Anim. Sci. (2001) 14:1138-1143.
Bosi, P. et al, "Spray-dried plasma improves growth performance and reduces inflammatory status of weaned pigs challenged with enterotoxigenic *Escherichia coli* K88," J. Anim. Sci. (2004) 82:1764-1772.
Bosworth, B T et al. "Identification of toxin and pilus genes in porcine *Escherichia coli* using Polymerase Chain Reaction (PCR) with multiple primer pairs," Abstracts of the 97th General Meeting of the Am Society for Microbiology, May 4-8, 1997.
Brosius, J et al, "Complete nucleotide sequence of a 16S ribosomal RNA gene from *Escherichia coli*," Proc Natl Acad Sci USA 75(10:4801-4805, Oct. 1978.
Brown, D. C. et al, "The influence of different management systems and age on intestinal morphology, immune cell numbers and mucin production from goblet cells in post-weaning pigs," Vet. Immunol. Immunopath (2006a) 111:187-198.
Brown, D. C. et al, "Ontogeny of T lymphocytes and intestinal morphological characteristics in neonatal pigs at different ages in the postnatal period," J. Anim. Sci. (2006b) 84:567-578.
Carr, D et al, "Excessive mortality in market-age turkeys associated with cellulitis," Avian Disease 40:736-741, 1996.
Cera, K. R. et al, "Effect of age, weaning and post-weaning diet on small intestinal growth and small intestinal morphology in young swine," J. Anim. Sci. (1988) 66:574.
Coffey, R. et al, "The impact of environment and antimicrobial agents on the growth response of early weaned pigs to spray-dried porcine plasma," J. Anim. Sci. (1995) 73:2532-2539.
Cooper, V, "Diagnosis of neonatal pig diarrhea," Vet Clinics N Am Food Animal Practice, 16(1):117-161 (2000).
"Immediate release" 'Online! Jan. 13, 2005, pp. 1-2 XP002342562, retrieved from the Internet: URL: http://www.agtechproducts.com/press/DSM_Market_Microsource.pdf>, p. 1, line 1-line 15, p. 2, paragraph 4-last paragraph. [source: PCT/US05/017141 ISR].
Cromwell, G. L., "Antimicrobial and promicrobial agents. In: A. J. Lewis and L. L. Southern (eds.)," Swine Nutrition. p. 611. CRC Press, Boca Raton, FL (2001).
Cruywagen, C. W. et al, "Effect of *Lactobacillus acidophilus* supplementation of milk replacer on preweaning performance of calves," J. Dairy Sci. (1996) 79:483-486.
Davis. M. E. et al, "Effect of direct-fed microbial and antibiotic supplementation on gastrointestinal microflora, mucin histochemical characterization, and immune populations of weanling pigs," Livestock. Sci. (2007) 108:249-253.
Davis, M.E. et al, "Comparison of direct-fed microbial and antibiotic supplementation on innate and adaptive immune characteristics of weaning pigs," Reprod. Nutr. Dev. (2006) 46(Suppl.1):S63.
Davis, M. E. et al, "Rearing environment affects T lymphocyte populations within the systemic circulation and the gastrointestinal tract of young pigs.," Experimental Biology meeting abstracts [on CD ROM]. (2005) The FASEB Journal, 19, Abstract #43.7.
Davis, M.E. et al. "Dietary supplementation with phosphorylated mannans improves growth response and modulates immune function in weanling pigs," J. Anim. Sci. (2004) 82:1882-1891.

Davis, M. E. et al, "Inhalation Toxicology in the Equine Respiratory Tract," In: Equine Respiratory Diseases, P. Lekeux. International Veterinary Information Service (2002).
Dean-Nystrom, E et al, "Edema disease: a re-emerging problem?," Am Assoc of Swine Veterinarians, pp. 223-224, 2001.
Donald, J, "Treating poultry house floors to improve performance," The Poultry Engineering, Economics & Management Newsletter, Issue No. 23, 4 pgs, May 2003.
Donovan, D. C., "Growth and health of Holstein calves fed milk replacers supplemented with antibiotics or enteroguard," J. Dairy Sci. (2002) 85:947-950.
Dritz, S. et al, "Growth and microbial flora of nonmedicated, segregated, early weaned pigs from a commercial swine operation," JAVMA (1996) 208:711.
Dunlop, R. H., "Pathogenesis of ruminant lactic acidosis," Adv. Vet Sci. Comp Med. (1972) 16:259.
Ecological Laboratories, "Microbe-Lift equine products," EQ1, EQ2 and EQ3 (May 2001) (1 pg).
Elam, C. J. "Acidosis in feedlot cattle: Practical observations," J. Anim. Sci. (1976) 43:898.
Fangman, T. et al, "Segregated early weaning," Swine Health Prod. (1997) 5:195.
Francis, D, "Post-weaning *E. coli*-diagnosis, treatment, control, and its effect on subsequent growth performance," Am Assoc of Swine Veterinarians, 495-499, 2004.
Fritts, C A et al, "*Bacillus subtilis* C-3102 (Calsporin) improves live performance and microbioligical status of broiler chickens," Applied Poultry Science, Inc., 9:149-155, 2000.
Fuller, R., "Introduction. In: R. Fuller (Ed.). Probiotics 2: applications and practical aspects," Chapman and Hall, New York. (1997) p. 1.
Gaskins, H. R., "Intestinal bacteria and their influence on swine growth In: Austin J. Lewis and Lee L. Southern (Ed.)," Swine Nutrition 2nd Edition. (2001) p. 585-608.
Gebert, S. et al, "Development of a direct fed microbial to control pathogens associated with turkey poult production," Poult. Sci. (2006) 85(suppl. 1):71.
Gebert, S. et al, "Effect of a Bacillus-based direct-fed microbial on turkey poult performance and changes within the gastrointestinal microflora," J. Anim. Sci. (2007) 85(suppl. 1):249.
Grimes, J L et al, "Heat treatment of turkey litter for reuse as bedding," Int J of Poultry Science 2(5):287-292, 2003.
Hammer, C. et al, "Characterization of a colostrum replacer and a colostrum supplement containing IgG concentrate and growth factors," J. Dairy. Sci. (2004) 87:106-111.
Hatheway, C. L. "Toxigenic Clostridia," Clinical Microbiology Reviews (1990) 3(1):66-98.
Hofacre, C L et al, "Subcutaneous Clostridial infection in broilers," Case Report, Avian Diseases vol. 30(3):620-622, 1986.
Hong, H. A. et al, "The use of bacterial spore formers as probiotics," FEMS Microbiol. Rev. (2005) 29:813-835.
Hungate, R. E. et al, "Microbiological and physiological changes associated with acute indigestion in sheep," Cornell Vet. (1952) 42:423.
Janstova, B. et al, "Heat Resistance of *Bacillus* spp. Spores Isolated form Cow's Milk and Farm Environment," ACTA Vet.. BRNO (2001) 70:179-184.
Jenny, B. F. et al, "Performance and fecal flora of calves fed a *Bacillus subtilis* concentrate," J. Dairy Sci. (1991) 74:1968-1973.
Jost B. H. et al, "Atypical cpb2 genes, encoding beta2-toxin in *Clostridium perfringens* isolates of nonporcine origin," Infect. Immun. (2005) 73:652-656.
/K/ "A multiple-strain product containing Bacillus strain BS 27 and strains other than those listed in the pending claims has been sold, at least as early as Jan. 1, 2000."
Karunakaran, D et al, "Use of antibiotics and its impact on gut microflora in turkeys," Am Avian Path, Philadelphia, PA, Aug. 2004.
Karunakaran, D, "Microbioligical challenges of commercial turkey flocks and methods of control," Poster #PP51 presented at AAAP Symposium on Poultry Vaccines and Vaccination Practices, Jul. 15-17, 2002.
Kennedy, C et al, "The A-toxin of *Clostridium septicum* is essential for virulence," Molecular Microbiology, 57(5): 1357-1366, 2005.

(56) References Cited

OTHER PUBLICATIONS

King, M. et al, "Terminal restriction fragment length polymorphism analysis of gastrointestinal bacteria from conventional and segregated early weaned pigs: colonization and succession of putative pathogens and potential direct fed microbials," J. Anim Sci. (2005) 83 (Suppl. 1): 197.
Kyriakis, S. C. et al, "The effect of probiotic LSP 122 on the control of post-weaning diarrhea syndrome of piglets," Res. Vet. Sci. (1999) 67:223-228.
La Ragione R M et al, "*Bacillus subtilis* spores competitively exclude *Escherichia coli* 078:K80 in poultry," Vet Microbiol 79:133-142, 2001.
La Ragione, R. M. et al, "Competitive exclusion by *Bacillus subtilis* spores of *Salmonella enterica* serotype Enteritidis and *Clostridium perfringens* in young chickens," Vet. Microbiol, (2003) 94:245-256.
Lu, J et al, "Diversity and succession of the intestinal bacterial community of the maturing broiler chicken," Applied and Environmental Microbiology, 69(11):6816-6824, Nov. 2003.
Marquardt, R et al, "Passive protective effect of egg-yolk antibodies against enterotoxigenic *Escherichia coli* K88+ infection in neonatal and early-weaned piglets," FEMS Immunology and Med Microbiology 23:283-288, 1999.
Marsh, T. et al, "Terminal restriction fragment length polymorphism analysis web-based research tool for microbial community analysis," Appl Environ Microbiol (2000) 66:3616-3620.
Maxwell, Jr., C. V. et al, "Feeding Weanling Pigs. In: Austin J. Lewis and Lee L. Southern (Ed.)," Swine Nutrition 2nd Edition. (2001) p. 691-717.
McCracken, B. A. et al, "Diet-dependent and diet-independent metabolic responses underlie growth stasis of pigs at weaning," J. Nutr. (1995) 125, 2838-2845.
McDonough, S. P., "Enteric pathogens in intensively reared veal calves," Am. J. Vet. Res. (1994) 55(11):1516-1520.
McMillan, K., "Foal pneumonia: An Illinois survey," An Health and Nutrit 34 (1986).
Morrill, J. L. et al, "Plasma proteins and a probiotic as ingredients in milk replacer," J. Dairy Sci. (1995) 78:902-907.
Mouricout, M. A. et al, "Inhibition of mannose-resistant haemagglutination of sheep erythrocytes by enterotoxigenic *Escherichia coli* in the presence of plasma glycoprotein glycans," FEMS Microbiol. Lett. (1986) 37:145-149.
Muir, L.A. et al, "Prevention of induced lactic acidosis in cattle by thiopeptin," J. Anim. Sci. (1981) 52:635.
Muyzer, G et al, "Profiling of complex microbial populations by denaturing gradient gel electrophoresis analysis of polymerase chain reaction-amplified genes coding for 16S rRNA," Applied and Environmental Microbiology, 59 (3):695-700, Mar. 1993.
Nagy, G et al, "Genetic diversity among *Escherichia coli* isolates carrying f18 genes from pigs with porcine postweaning diarrhea and edema disease," J Clinical Microbiology 37:5:1642-1645, May 1999.
Niilo, L., "*Clostridium perfringens* in animal disease: a review of current knowledge," Can. Vet. J. (1980) 21:141-148.
Nollet, H. et al, "Protection of just weaned pigs against infection with F18+ *Escherichia coli* by non-immune plasma powder," Vet. Microbiol. (1999) 65:37-45.
"Nonruminant Nutrition: weanling Pigs-additives" Online! 2004, pp. 25-28 XP002342561, Retrieved from the Internet: URL:http//www.fass.org/2004/abstracts/25.PDF> p. 26, col. 2, paragraph 3-5 [source: PCT US2005/017141 ISR].
Owens, F. N. et al, "Acidosis in cattle: a review," J. Anim. Sci. (1998) 76:275-286.
Parrott, D et al, "Molecular typing of hermolytic *Escherichia coli* isolated from swine," Paper 385 (1 pg), Intl Pig Vet Soc, 2002.
Patterson, J A et al, "Application of prebiotics and probiotics in poultry production," Poultry Science 82:626-631, 2003.
Perez-Bosque, A. et al, "Dietary plasma protein affects the immune response of weaned rats challenged with *S. aureus*," Superantigen B. J. Nutr. (2004) 134:2667-2672.
Power, E. G., "RAPD typing in microbiology—a technical review," J. Hosp. Infect. (1996) 34(4):247-265.
Rehberger, T, "Genome analysis of *Propionibacterium freudenreichii* by pulsed-field gel electrophoresis," Current Microbiology 27(1):21-25 Jul. 1993 (abstract).
Roche, K. C. et al, "Transforming growth factor beta-1 ameliorates intestinal epithelial barrier disruption by *Cryptosporidium parvum* in the absence of mucosal T lymphocytes," Infect. Immun. (2000) 68:5635-5644.
Roe, S, "Protein purification techniques," 2d Ed. Oxford U. Press, 172-175 (2001).
Slyter, L.L., "Influence of acidosis on rumen function," J. Anim. Sci. (1976) 43:910.
Snoeyenbos, G H, "Protecting chicks and poults from Salmonellae by oral administration of "normal" gut microflora," Avian Diseases 22(2):273-287, 1977.
Songer, J. G., "Clostridial enteric diseases of domestic animals," Clinical Microbiology Reviews (1996) 9(2):216-234.
"Table of Contents" Online! 2004, p. 1-4, XP002342560, retrieved from the Internet: URL:http://www.fass.org/2004/abstracts/>, p. 1, lines 1-14 [source: PCT/US05/017141 ISR].
Tam, N. K. M. et al, "The intestinal life cycle of *Bacillus subtilis* amd close relatives," J. Bacteriol. (2006) 188:2692-2700.
Tang et al, "Effect of segregated early weaning on postweaning small intestinal development in pigs," J. Anim. Sci. (1999) 77:3191.
Tanner, M. K. et al. "Respiratory and environmental effects of recycled phone book paper versus sawdust as bedding for horses," J Eq Vet Sci (1998) 468-476.
Tannock, G. W., "A special fondness for lactobacilli," Appl. Environ, Microbiol. (2004) 70:3189-3194.

\* cited by examiner

METHODS OF CONTROLLING PIT FOAM

CROSS-REFERENCE TO RELATED APPLICATIONS

This application claims priority under 35 U.S.C. §119(e) to U.S. Provisional Patent Application No. 61/345,925, filed May 18, 2010, the entirety of which is incorporated by reference herein.

BIBLIOGRAPHY

Complete bibliographic citations of the references referred to herein by the first author's last name and publication year in parentheses can be found in the Bibliography section.

FIELD OF THE INVENTION

The invention relates to methods for controlling foam that forms on manure storage units, such as manure pits.

DESCRIPTION OF THE RELATED ART

Swine production facilities in the Midwest typically house animals in pens with slatted floors over a deep pit into which manure is collected and stored. Deep pit systems collect manure in the swine barn under the pens and store the accumulated manure over an approximately six month period of time, after which manure from deep pits is pumped and applied as fertilizer over cultivated land. Storage of swine manure under these anaerobic conditions results in emissions of gaseous compounds, such as methane and hydrogen sulfide, from anaerobic microbial fermentation of manure substrates. Processing of livestock manure under anaerobic conditions is a process in which microorganisms convert the organic material in manure to methane and carbon dioxide gases. Thereby the functional capability of the methanogen population is a crucial factor determining how well the anaerobic decomposition process occurs (Wolfe, 1971).

The production of methane and carbon dioxide by methanogens is a four-step process including hydrolysis, acidogenesis, acetogenesis, and methanogenesis (Bernet and Beline, 2009). To prevent malodorous compounds the production of acids by bacteria in the manure pit must be in equilibrium with the consumption of these acids by methanogens (Zho, 2000). In this redox reaction, volatile fatty acids resulting from the digestion of organic waste material by bacteria are metabolized with carbon acting as the terminal electron acceptor through anaerobic respiration by methanogens to form methane and carbon dioxide. When this chemical process is in disequilibrium, such as when the production of acids by bacteria overwhelms the capacity of the methanogens to perform methanogenesis (Gonzalez-Fernandez et al., 2009), sulfate becomes the terminal electron acceptor to form hydrogen sulfide via sulfate-reducing bacteria.

Intensive swine production systems often present a challenge to the proper function of anaerobic manure storage systems due to overloading of the manure pit, weather constraints that may prevent land application of stored manure, and feeding management practices. Often manure holding pits become overloaded with organic waste material and overwhelm the capacity of methanogens to produce methane, resulting in the formation of hydrogen sulfide gas. Recently, swine production facilities, particularly those with manure holding pits under pens in swine barns, have been experiencing a new problem in which large quantities of thick foam is forming on the surface of the manure pits. This foam formation decreases manure pit capacity as foam rises up through the slatted floors and comes in contact with animals. This foam has been implicated in flash fire explosions due to the propensity of the foam layer to trap flammable gases such as methane and hydrogen sulfide. The dangers of gas expressed from swine manure pits during agitation and pumping have been documented (Hoff et al., 2006). The trapping of these gases by foam formation on the pit surface has exacerbated the hazard. The foaming pit problem in the swine industry has been identified and discussed by Dr. Mike Brumm in his Nov. 14, 2008 blog entry, and he has recently reported an increase in foaming pit incidences and the dangers associated with the trapping of explosive gas by the foam during the fall pit pumping season in an Oct. 19, 2009 entry (Brumm, 2009).

It is unknown why the incidences of excessive foaming in swine manure pits are becoming more prevalent. A relatively small extent of foaming in waste storage and processing systems is quite common as a consequence of associations between microbial activity resulting in gas formation and surface tension at the liquid face. This biological foaming is a fairly common nuisance in municipal wastewater treatment plants and seems to be associated with seasonal warmer temperatures (Pujol et al., 1991; Soddell and Seviour, 1995). The bacterial organisms associated with foam formation in municipal wastewater treatment plants have been fairly well characterized and are mainly filamentous bacteria of the phylum *Actinobacteria*, most commonly of the genera *Gordonia, Nocardia, Rhodococcus*, and *Skermania* (Bitton, 1994; Soddell, 1999). The filamentous bacteria have hydrophobic cell walls and most have the capability to produce surfactants (Lemmer, 1986; Pagilla et al., 2002). Many have suggested that the association of the filamentous bacteria to foam affords the organisms a selective advantage such that the foam provides a supply of nutrients in the form of hydrophobic substrates at the air/water interface (Lemmer, 1986; Soddell, 1999). It has been reported that growth of *Actinomycetes* in sewage treatment plants is enhanced when these organisms have access to high levels of hydrophobic substrates in the form of grease and oil (Lemmer and Baumann, 1988), and high lipid loading rates have been associated with biological foaming in wastewater treatment systems (Frigon et al., 2006). Additionally, foaming in anaerobic digesters has been reported to invert the solids profile, such that higher solids are observed at the top of the digester instead of at the bottom as is the case in the absence of foaming (Pagilla et al., 1997).

Several studies have characterized the microbial community in anaerobic swine manure storage facilities and have identified the predominant bacteria present to be the *Eubacterium, Clostridium, Bacillus-Lactobacillus-Steptococcus, Mycoplasma, and Bacteroides-Prevotella* groups (Peu et al., 2006; Snell-Castro et al., 2005; Whitehead and Cotta, 2001). Although the filamentous bacteria identified in municipal wastewater treatment plants do not seem to be present in swine manure storage facilities, these organisms are present in aerobic environments and may be present in swine manure holding facilities only near the surface of the liquid slurry and do not represent predominant populations that would be detectable in the anoxic conditions predominant in swine manure slurry. Also, these studies characterized the microbial community from slurry samples from swine manure pits, not samples obtained near the liquid surface strictly from foaming swine manure. Data from our laboratory characterized differences in the microbial community between foaming and non-foaming swine deep-pit manure systems and found nine terminal restriction fragments that were more abundant in samples from foaming pits and 12 terminal restriction fragments more abundant in manure pits without foam (Rehberger et al., 2009).

It is not known whether the microbial populations associated with foaming swine manure pits and municipal wastewater treatment plants are similar. Swine nutrition changes have occurred over the last five years that have resulted in changes in swine manure composition that are similar to conditions that are associated with foaming blooms in the better characterized municipal wastewater treatment plants.

The greatest change in swine diet formulations recently has been the dramatic increase in the use of dried distiller's grains with solubles (DDGS), a byproduct of the ethanol production industry. Estimates indicate that the use of DDGS increased from 0.75 million metric tons in 2003 to 3 million metric tons in 2008, with usage doubling from 2007 to 2008 (Shurson, 2009). Use of DDGS in swine diets has been shown to increase the total fecal excreta (Fu et al., 2004), and this increase in fecal output is likely resulting in an overloading of substrate in swine manure pit systems. Also, the concentration of protein, fat and fiber is approximately three times greater in DDGS compared to corn (NRC, 1998) due to the conversion of starch to ethanol in the fermentation process. However, the digestibility of these nutrients is less than that of corn (Stein and Shurson, 2009), such that a greater amount of undigested nutrients are excreted into swine manure pits.

Previous treatment applications to alleviate foam on the surface of swine manure pits have mimicked those used by the municipal wastewater treatment plants to combat the problem, and consist primarily of defoaming agents with low viscosity that break up air bubbles and release entrapped air. These defoamers usually contain oil, silicone or polyethylene glycol/polypropylene glycol polymers as a primary active ingredient. Some swine producers experiencing foaming problems in their swine barns have used water sprinklers to break up the surface foam and there are reports that some have resorted to the use of diesel fuel for this purpose (Brumm, 2009). Each of these solutions have reported some efficacy for breaking down surface foam and providing a transient solution; however, they do not control the biological process of foam formation. Microbial additions to alleviate foaming in wastewater treatment plants have been reported, but information to support their validity in controlling foaming episodes is limited and continuous application of these products in municipal treatment facilities is impractical (Soddell and Seviour, 1990). While the superficial symptom of foam can be briefly checked, foam quickly forms again as these solutions offer no long-term remedy for the underlying processes resulting in the foaming swine pit problem.

SUMMARY OF THE INVENTION

The invention, which is defined by the claims set out at the end of this disclosure, is intended to solve at least some of the problems noted above. A method of controlling foam in a manure pit is provided. In the method, one or more *Bacillus* strain(s) is administered in an effective amount to animals whose manure is stored in the manure pit.

In at least some embodiments, the *Bacillus* strains include *B. licheniformis* 842 (NRRL B-50516) or a strain having all of the identifying characteristics of the *B. licheniformis* 842 (NRRL B-50516); *B. subtilis* 27 (NRRL B-50105) or a strain having all of the identifying characteristics of the *B. subtilis* 27 (NRRL B-50105); and *B. licheniformis* 21 (NRRL B-50134) or a strain having all of the identifying characteristics of the *B. licheniformis* 21 (NRRL B-50134). Administering the combination of strains controls foam in the manure pit.

In at least some embodiments, the *Bacillus* strain is *B. subtilis* LSSAO1 (NRRL B-50104) or a strain having all of the characteristics of the *B. subtilis* LSSAO1 (NRRL B-50104).

Another method is provided for controlling foam in a manure storage unit. In the method, *B. subtilis* LSSAO1 (NRRL B-50104) or a strain having all of the characteristics of the *B. subtilis* LSSAO1 (NRRL B-50104) is administered in an effective amount to the manure storage unit.

Another method of controlling foam in a manure pit is provided. In the method, *Bacillus* strains in an effective amount are administered to pigs whose manure is stored in the manure pit. The *Bacillus* strains comprise *B. licheniformis* 842 (NRRL B-50516) or a strain having all of the identifying characteristics of the *B. licheniformis* 842 (NRRL B-50516); *B. subtilis* 27 (NRRL B-50105) or a strain having all of the identifying characteristics of the *B. subtilis* 27 (NRRL B-50105); and *B. licheniformis* 21 (NRRL B-50134) or a strain having all of the identifying characteristics of the *B. licheniformis* 21 (NRRL B-50134).

BRIEF DESCRIPTION OF THE DRAWINGS

Exemplary embodiments of the invention are illustrated in the accompanying drawings.

Figure 1A:
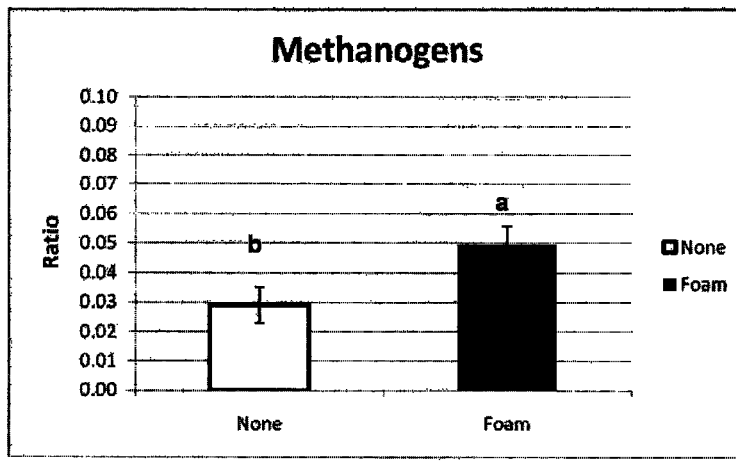
FIGS. 1A-1B are graphs showing quantity of methanogens in samples from swine deep-pit manure storage systems with and without foam (FIG. 1A) and from foam and liquid samples obtained from three foaming swine deep-pit manure storage units (FIG. 1B). Data is expressed as a ratio of methanogen DNA relative to total prokaryote DNA in each sample as measured by delta Ct values analyzed by quantitative real-time PCR. [a,b] Means without similar letters are significantly different (P<0.05). [c,d] Means without similar letters are significantly different (P=0.08).
Figure 1B:
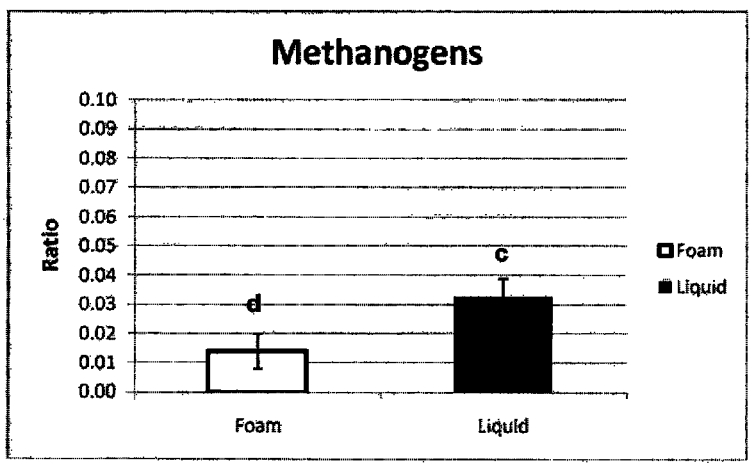

Before explaining embodiments of the invention in detail, it is to be understood that the invention is not limited in its application to the details of construction and the arrangement of the components set forth in the following description or illustrated in the drawings. The invention is capable of other embodiments or being practiced or carried out in various ways. Also, it is to be understood that the phraseology and terminology employed herein is for the purpose of description and should not be regarded as limiting.

DETAILED DESCRIPTION

Provided herein are methods of using *Bacillus* strains for controlling foaming manure pits. Preliminary data gathered from commercial swine farms suggests that high DDGS diets result in greater levels of nutrient excretion in deep-pit manure holding facilities. This nutrient overload is likely altering microbial ecology in the manure pit ecosystem in such a manner that is conducive to biological foaming episodes.

It has been discovered that certain *Bacillus* strains can be used to control foaming in manure pits. In one embodiment, an effective amount of a multiple-strain direct-fed microbial (DFM) is administered to an animal. The DFM contains *Bacillus* strains *Bacillus subtilis* 27 ("BS 27"; (NRRL B-50105)), *Bacillus licheniformis* (previously thought to be *B. amyloliquefaciens*) 842 ("*B. licheniformis* 842"; (NRRL B-50516)), and *Bacillus licheniformis* 21 ("B1 21"; (NRRL B-50134)).

*B. subtilis* strain 27 was deposited on Jan. 24, 2008 at the Agricultural Research Service Culture Collection (NRRL), 1815 North University Street, Peoria, Ill., 61604 and given accession number NRRL B-50105. On Apr. 15, 2008, *B. licheniformis* strain 21 was deposited at NRRL and given accession number NRRL B-50134. On May 20, 2011, B. licheniformis 842 was deposited at NRRL and given accession number NRRL B-50516.

In another embodiment, a single-strain direct-fed microbial (DFM) that includes *B. subtilis* LSSAO1 is used. Strain LSSAO1 was deposited on Jan. 22, 2008 at the Agricultural Research Service Culture Collection (NRRL), 1815 North University Street, Peoria, Ill., 61604 and given accession number NRRL B-50104. All of these deposits were made under the provisions of the Budapest Treaty on the International Recognition of the Deposit of Microorganisms for the Purposes of Patent Procedure.

The strains in the DFMs have been selected based on their ability to shift nutrient utilization by the microbial population and subsequently alter the microbial ecology such that aggregated foaming incidents are alleviated, either by lessening gas production available to be trapped in the foam matrix, altering the availability of molecular compounds making up the foam matrix, or directly inhibiting the growth of bacteria associated with foaming incidents.

Strains having all of the identifying characteristics of these strains can also be used.

In one embodiment of the multiple-strain *Bacillus*-based DFM, the strains are administered in the following amounts. However, other amounts can also be used. 70% of the total CFUs for the *Bacillus* strains of B. licheniformis 842 (NRRL B-50516) or a strain having all of the identifying characteristics of the B. licheniformis 842 (NRRL B-50516); 10% of the total CFUs for the *Bacillus* strains of *B. subtilis* 27 (NRRL B-50105) or a strain having all of the identifying characteristics of the *B. subtilis* 27 (NRRL B-50105); and 20% of the total CFUs for the *Bacillus* strains of *B. licheniformis* 21 (NRRL B-50134) or a strain having all of the identifying characteristics of the B. licheniformis 21 (NRRL B-50134).

Making and Using the *Bacillus*-Based Direct-Fed Microbials:

The *Bacillus* strains are grown in a liquid nutrient broth. In at least one embodiment, the *Bacillus* strains are grown to a level at which the highest number of spores are formed.

The *Bacillus* strains are produced by fermentation of the bacterial strains. Fermentation can be started by scaling-up a seed culture. This involves repeatedly and aseptically transferring the culture to a larger and larger volume to serve as the inoculum for the fermentation, which is carried out in large stainless steel fermentors in medium containing proteins, carbohydrates, and minerals necessary for optimal growth. A non-limiting exemplary medium is TSB. After the inoculum is added to the fermentation vessel, the temperature and agitation are controlled to allow maximum growth. Once the culture reaches a maximum population density, the culture is harvested by separating the cells from the fermentation medium. This is commonly done by centrifugation.

In one embodiment, to prepare the *Bacillus* strains, each *Bacillus* strain is fermented between a $5 \times 10^8$ CFU/ml level to about a $4 \times 10^9$ CFU/ml level. In at least one embodiment, a level of $2 \times 10^9$ CFU/ml is used. The bacteria are harvested by centrifugation, and the supernatant is removed. In at least some embodiments, the pelleted bacteria are freeze-dried and mixed with a carrier. However, it is not necessary to freeze-dry the *Bacillus* before using them. The strains can also be used with or without preservatives, and in concentrated, unconcentrated, or diluted form.

The count of the culture can then be determined. CFU or colony forming unit is the viable cell count of a sample resulting from standard microbiological plating methods. The term is derived from the fact that a single cell when plated on appropriate medium will grow and become a viable colony in the agar medium. Since multiple cells may give rise to one visible colony, the term colony forming unit is a more useful unit measurement than cell number.

To prepare direct-fed microbials described herein, the cultures and carriers (where used) can be added to a ribbon or paddle mixer and mixed for about 15 minutes, although the timing can be increased or decreased. The components are blended such that a uniform mixture of the cultures and carriers result. The final product is preferably a dry, flowable powder. The bacteria can then be added to animal feed or a feed premix.

A multiple-strain DFM containing *Bacillus* strains or a single *Bacillus* strain can be administered to animals, such as pigs. In some embodiments, an effective amount of a multiple-strain DFM containing *Bacillus* strains or a single *Bacillus* strain is administered to the animal by supplementing food intended for the animal with an effective amount of at least one strain of bacterium. In one embodiment, the DFM is added to the animals' feed at a rate of at least about $7.9 \times 10^4$ CFU per gram of feed. In other embodiments, the DFM is added to the animals' feed at a rate of at least about $8.7 \times 10^4$ CFU per gram of feed or at least about $8.8 \times 10^4$ CFU per gram of feed. In additional embodiments, the DFM is added to the animals' feed at a rate of at least about $1.0 \times 10^5$ CFU per gram of feed.

By "effective amount," is meant a quantity of DFM sufficient to allow improvement, i.e., reduction in the amount of foam production in comparison with a reference. The foam reductive effect can be measured as described herein or by other methods known in the art. This effective amount can be administered to the animal by providing ad libitum access to feed containing the DFM. The DFM can also be administered in one or more doses.

The multiple-strain DFM, as well as the single-strain DFM, can also be added to an animal's drinking water, top dressed onto the animal's feed, or administered in other ways.

For both the multiple-strain DFM, as well as the single-strain DFM, on a CFU/pig/day basis, in one embodiment, the DFM is administered to the animal at a rate of at least about $2.0 \times 10^8$ CFU/pig/day. In another embodiment, the DFM is administered to the animal at a rate of at least about $2.2 \times 10^8$ CFU/pig/day. In additional embodiments, the DFM is administered to the animal at a rate of at least about $2.5 \times 10^8$ CFU/pig/day.

When fed to an animal, the *Bacillus* strains in the DFM are excreted into the manure. This inoculates deep-pit manure holding systems via fecal excretion of the efficacious organisms of the DFM.

In addition, one or more *Bacillus* strain(s) can be added directly to a manure storage unit, including, but not limited to, a manure pit or an anerobic digester, to treat or control foaming. In one embodiment, the one or more *Bacillus* strain(s) is added to a manure pit at a rate of at least about $4.4 \times 10^4$ CFU/ml of the manure. In another embodiment, the one or more *Bacillus* strain(s) is added to a manure pit at a rate of at least about $1.0 \times 10^5$ CFU/ml of the manure.

EXAMPLES

The following Examples are provided for illustrative purposes only. The Examples are included herein solely to aid in a more complete understanding of the presently described invention. The Examples do not limit the scope of the invention described or claimed herein in any fashion.

Example 1

Differences in Fecal Nutrient Output Between Pigs Fed Dried Distillers Grains with Solubles (DDGS) Compared to Pigs Fed Standard Corn-Soybean Meal-Based Diets Diets formulated with regular DDGS or high-protein DDGS were compared to corn-soybean meal-based diets typically fed in the swine industry to growing-finishing pigs in a large, integrated commercial swine system. The two types of DDGS were included in the diets at a 30% inclusion level and all diets were formulated to meet similar nutrient specifications. Fecal samples were obtained from pigs in two DDGS feeding trials evaluating the inclusion of regular DDGS and high-protein DDGS. In both trials, animals were housed in pens with twenty-five (25) pigs per pen. Pigs in three pens each representing the control and regular DDGS diets (six total pens) were sampled for nutrient analyses in the first study, whereas five pens each were sampled representing the control and high-protein DDGS in a separate experiment. Three (3) individual fecal samples were collected from each pen after seven (7) days of feeding the experimental diets in both experiments.

Nutrient compositions of samples representing the experimental diets were analyzed to illustrate the alteration in fecal nutrient excretion resulting from the inclusion of high levels of DDGS in swine diets. Fecal samples from pigs fed diets containing 30% regular DDGS had higher (P>0.01) Neutral detergent fiber (NDF) and tended to have higher (P=0.06) Acid detergent fiber (ADF) than those from pigs fed typical corn-soybean meal diets (Table 1). When pigs were fed diets containing 30% of the high-protein DDGS, fecal nutrient excretion of crude protein and total Kjeldahl nitrogen was greater (P<0.01) when pigs were fed the high protein DDGS compared to those fed typical corn-soybean meal diets (Table 2). Although not statistically different, ADF and NDF were numerically higher in fecal samples from pigs fed the high protein DDGS compared to those fed corn-soybean meal diets, as was the case when regular DDGS were fed. Additionally, fecal samples from pigs fed the high protein DDGS had greater (P<0.01) levels of fiber-bound protein (ADFProtein; Table 2) than pigs fed corn-soybean meal diets.

TABLE 1

Fecal nutrient concentrations of pigs fed a diet containing 30% "regular" DDGS compared to pigs fed a control diet devoid of DDGS.[1]

|  | Control | 30% DDGS | SEM | P = |
|---|---|---|---|---|
| Moisture | 73.85 | 73.64 | 0.45 | 0.758 |
| DM | 26.15 | 26.36 | 0.45 | 0.758 |
| TKN | 3.99 | 3.71 | 0.13 | 0.215 |
| Protein | 24.94 | 23.21 | 0.83 | 0.215 |
| ADF | 19.20 | 21.13 | 0.54 | 0.064 |
| NDF | 46.36 | 50.49 | 0.49 | 0.003 |
| ADFProtein | 2.77 | 2.67 | 0.19 | 0.717 |

[1]Values are the means of three samples representing each treatment.

TABLE 2

Fecal nutrient concentrations of pigs fed a diet containing 30% high-protein DDGS compared to pigs fed a control diet devoid of DDGS.[1]

|  | Control | 30% HPDDGS | SEM | P = |
|---|---|---|---|---|
| Moisture | 73.30 | 71.72 | 0.67 | 0.134 |
| DM | 26.70 | 28.28 | 0.67 | 0.134 |
| TKN | 3.84 | 4.31 | 0.08 | 0.004 |
| Protein | 23.61 | 26.93 | 0.48 | 0.001 |
| ADF | 20.25 | 21.12 | 0.78 | 0.457 |
| NDF | 54.12 | 56.01 | 2.29 | 0.575 |
| ADFProtein | 2.39 | 3.56 | 0.19 | 0.002 |

[1]Values are the means of five samples representing each treatment

These data demonstrate that the fecal nutrient output of pigs fed diets containing DDGS is altered compared to corn-soybean meal based diets that were normally fed to pigs in the recent past. Specifically, the quantity of the fibrous component of the fecal matter excreted and the nitrogen component bound to the fiber is increased, resulting in an alteration in the nutrient quantity and profile present in the deep pit manure storage systems.

Example 2

Differences in Nutrient Composition of Swine Manure Samples Between Foaming and Non-Foaming Deep Pit Storage Systems Manure samples from deep pit storage systems with and without foam were collected at various sites from three production systems and the nutrient composition of these samples was assessed. Manure samples were obtained by sampling the entire depth of the manure storage pit with a 6'-long PVC sampling rod and classified as having none, low, or high levels of foam and were defined as follows: None=less than 1.0 inches of foam on the manure surface (n=30), Low=1.0 to 6.0 inches of foam on the manure surface (n=25), and High=greater than 6.0 inches of foam on the manure surface (n=14). Manure samples obtained from deep-pit storage systems with a high degree of foaming had greater (P<0.05) concentrations of fiber-bound protein (ADFProtein) compared to manure samples from non-foaming pits and those with a low degree of foam (Table 3). The concentration of ADFProtein in manure pits with a high degree of foaming was very similar to the concentration measured in fecal samples obtained from pigs fed diets containing 30% of high-protein DDGS (Table 2). Also, manure samples from pits with a high degree of foaming and samples from manure pits without foaming had greater (P<0.05) crude fat composition than samples from manure pits with a low degree of foaming (Table 3).

TABLE 3

Nutrient concentration of samples from deep pit manure storage systems with low and high levels of foaming compared to pits with no foam.

| | Foaming Level[1] | | | | |
|---|---|---|---|---|---|
| | None | Low | High | SEM | P = |
| Moisture | 91.74 | 92.52 | 93.48 | 0.51 | 0.062 |
| Crude fat | 14.62[a] | 8.82[b] | 12.40[a] | 1.18 | 0.001 |
| Crude protein | 53.66 | 61.53 | 60.66 | 3.11 | 0.117 |
| Ammonia N | 6.11 | 6.79 | 6.87 | 0.40 | 0.301 |
| ADF | 17.01 | 17.22 | 17.69 | 0.68 | 0.766 |
| NDF | 38.44 | 37.40 | 32.01 | 2.15 | 0.073 |
| ADFProtein | 2.65[c] | 2.95[b] | 3.66[a] | 0.14 | 0.001 |

[1]Foam levels are defined as: None = less than 1.0 inches of foam on manure surface (n = 30); Low = 1 inch to 6 inches of foam on the manure surface (n = 25); High = greater than 6 inches of foam on the manure surface (n = 14). Highest level of foam on the surface of manure pits samples was 48 inches.
[a,b,c]Means without common superscripts differ, P < 0.05.

Example 3

Differences in Nutrient Composition Between Liquid Manure and Foam Samples from Foaming Swine Deep Pit Manure Systems Samples were obtained representing the liquid portion and the foam on top of three deep-pit swine manure storage systems experiencing foaming and nutrient analyses were performed. The concentration of crude fat was higher (P<0.05) in foam samples compared to samples of the liquid portion of the deep-pit manure storage system, as were concentrations of copper, iron, and zinc (Table 4). These data suggest that lipid content of the deep-pit manure system may have a role in foam formation on the surface of swine manure pits, similar to its role as a water-surface interface for nutrient acquisition by filamentous bacteria associated with foaming in municipal wastewater treatment plants. Furthermore, the high presence of minerals in the foam that would normally be concentrated in the solids component at the bottom of the pit indicates an inversion of the solids profile that has been shown to occur in anaerobic digesters experiencing foaming.

TABLE 4

Nutrient and mineral composition of foam samples and liquid manure samples obtained from three deep pit manure storage systems experiencing foaming.

| | Manure Sample | | | |
|---|---|---|---|---|
| | Liquid | Foam | SEM | P = |
| Moisture | 93.11 | 90.90 | 2.92 | 0.579 |
| Crude fat | 8.71 | 28.94 | 3.46 | 0.037 |
| Crude protein | 71.45 | 50.41 | 19.96 | 0.458 |
| Ammonia N | 8.24 | 4.01 | 3.22 | 0.373 |
| ADF | 16.67 | 12.00 | 5.35 | 0.529 |
| NDF | 35.17 | 15.30 | 11.60 | 0.276 |
| ADFProtein | 3.77 | 4.43 | 0.73 | 0.516 |
| Mineral composition | | | | |
| Calcium | 1.66 | 2.19 | 0.41 | 0.375 |
| Phosphorus | 2.51 | 2.66 | 0.22 | 0.616 |
| Potassium | 4.83 | 3.09 | 1.65 | 0.459 |
| Magnesium | 1.40 | 1.58 | 0.11 | 0.292 |
| Sodium | 1.13 | 0.71 | 0.36 | 0.413 |
| Sulfur | 1.36 | 2.04 | 0.18 | 0.084 |
| Aluminum | 428.33 | 410.00 | 118.33 | 0.906 |
| Copper | 393.67 | 705.00 | 57.01 | 0.042 |
| Iron | 2487.67 | 3650.00 | 192.80 | 0.035 |
| Manganese | 409.00 | 473.00 | 72.67 | 0.525 |
| Zinc | 2074.00 | 3829.00 | 374.15 | 0.056 |

[1]Samples from the liquid and foam portion of each deep pit manure storage system were obtained. Values represent the mean of three liquid manure samples and 3 foam samples.

Example 4

Isolation and Identification of Gastrointestinal Bacteria in Samples from Foaming and Non Foaming Deep Pit Swine Manure Storage Systems Sample Processing and DNA Isolation.

Samples obtained from deep pit swine manure storage systems and foam samples were combined with 10 mL of sterile tryptic soy broth (TSB)+10% glycerol broth and frozen at −20° C. until subsequent DNA isolation. Frozen samples were thawed on ice prior to DNA isolation. Solutions were vortexed for 30 seconds to yield a heterogeneous sample. Genomic DNA was extracted from one mL of each pit sample using a traditional phenol-chloroform isolation procedure. The resulting genomic DNA was further purified using the High Pure PCR Template Preparation Kit (Roche Applied Sciences).

PCR Amplification and Terminal-Restriction Length Polymorphism (T-RFLP) Analysis.

Amplification reactions using 2 µL of purified genomic DNA from each sample were performed in triplicate to provide adequate quantity of amplified product and to reduce PCR variation. PCR amplification of a large portion of the 16S ribosomal RNA gene coding region was carried out using a 5'-tetrachlorofloursciene labeled eubacterial 16S forward primer 8F (AGAGTTTGATYMTGGCTCAG) and the universal reverse primer 785R (ACTACCRGGG-TATCTAATCC). Reaction mixtures of 50 µL contained 1×PCR buffer, each deoxynucleoside triphosphate (dNTP) at a concentration of 280 µM, 1.5 mM $MgCl_2$, 12.5 pM of tetramethylammonium chloride (TMAC), 50 pM of each primer and 2.5 U of Platinum Taq (Invitrogen, Madison, Wis.). Positive and negative controls were included to monitor the effects of contaminating DNA found in commercial Taq enzymes. PCR conditions were 95° C. for 5 minutes, 30 cycles of denaturation at 95° C. for 30 seconds, annealing at 55.0° C. for 30 seconds, and extension at 72° C. for 120 seconds. The final cycle included a final extension at 72° C. for 7 minutes. Purity of PCR products was verified by running in a 1% agarose gel, staining with ethidium bromide and visualizing with an ultraviolet transilluminator. Fluorescently labeled PCR amplicons that were performed in triplicate from each sample were pooled and then purified from the primers and concentrated to 80 µL using a Qiagen PCR Clean Up Kit (Qiagen, Valencia, Calif.).

Subsequently, the cleaned sample was split into four equal volumes. Three of the aliquots were then digested individually with 10 units of either BstUI at 60° C. HaeIII, or MspI individually at 37° C. for 4 hours. Terminal restriction fragments (TRFs) from digestions using the restriction enzyme BstUI are denoted by the letter U followed by the size of the fragment, e.g. U100.79, while the H was used to designate TRFs from digestions using the restriction enzyme HaeIII and M for the restriction enzyme MspI. The use of three restriction enzymes improved the possibility of taxonomic identification of each TRF to the fewest number of bacterial species. DNA was analyzed using an ABI 3730xl capillary sequencer (Applied Biosystems) using GeneMapper 4.0 software (High-Throughput Sequencing and Genotyping Unit, Urbana, Ill. TRFs with sizes outside of the ranges of 20-785 basepairs and TRFs with peak heights below 50 relative fluorescence units were removed from the analysis.

Identification of Bacteria by TRF Matching.

Sample T-RFLP data from each individual sample was imported into the Bionumerics Gel Compar II package using the specialized T-RFLP extension (Applied Maths, Austin, Tex.). The Gel Compar II program was used to facilitate accurate band matching for all three restriction enzymes using a 1.0% position tolerance to define the bacterial species identified as OTUs by TRFs derived from the three restriction enzymes.

Example 5

Differences in Microbial Populations Between Manure Samples from Foaming and Non-Foaming Swine Deep Pit Manure Systems Manure samples from deep pit storage systems with and without foam were collected at various sites from three production systems and the microbial communities of these samples were assessed by T-RFLP analysis. Manure samples at each site were obtained and classified as in Example 2.

Foaming pit samples had a greater abundance (P<0.05) of *Alphaproteobacteria, Betaproteobacteria, Deltaproteobacteria*, and *Actinobacteria* compared to non-foaming pit samples, as putatively identified by the following TRFs: U87.01, U187.38, U227.63, U230.37, H255.87, H274.78, M124.72, M24615, and M248.14. Furthermore, some of these TRFs in greater abundance in foaming pits were putatively identified as sulfur-reducing bacteria and methanogens (U187.38, H274.78, M246.15, and M248.14). Differences in the sulfur-reducing bacteria and methanogen populations in foaming swine deep pit manure storage systems support the concept that nutrient overloading in swine deep pit manure systems is disrupting microbial ecology and the microbial balance for anaerobic digestion equilibrium.

Example 6

Differences in Microbial Populations between Samples Representing the Liquid Portion and the Foam on Top of Swine Deep Pit Manure Systems Experiencing Foaming Samples were obtained representing the liquid portion and the foam on top of three deep-pit swine manure storage systems experiencing foaming, and T-RFLP analyses were performed. T-RFLP analysis revealed the predominate microbial populations in the liquid portion of the foaming manure pits sampled included *Proteobacteria* and *Actinobacteria*, as TRFs representing these classifications (TRFs U215.01 and M275.76 derived by 8F primer with BstUI and MspI restriction enzyme digest, respectively; TRFs M192.66 and M301.03 derived by 785r primer with MspI restriction enzyme digest) were more predominant (P<0.05) in liquid samples compared to foam. These TRF classifications were similar to those observed in samples representing the entire liquid depth from the deep pit swine manure storage facilities. TRFs that were identified in greater abundance in foam samples compared to the liquid portion were putatively identified as Flexibacter, a classification that includes filamentous bacteria that have been associated with foaming in municipal wastewater treatment plants. These findings lend credence to the concept that foam formation provides a biological niche for specific populations of bacteria distinct from populations present in the liquid portion of anaerobic deep pit swine manure storage systems.

Example 7

Quantitative Analysis of Sulfate-Reducing Bacteria and Methanogens in Manure Samples from Foaming and Non-Foaming Deep Pit Swine Manure Storage Systems Because methane gas from anaerobic digestion is most likely resulting in foaming conditions of deep pit swine manure storage systems and sulfate-reducing bacteria will likely be a larger component of the microbial community when anaerobic decomposition is disrupted, these archea were evaluated and compared between samples from foaming and non-foaming deep pit swine manure storage units. Relative quantities of sulfate-reducing bacteria were not different between swine manure pits with and without foam, or between foam and liquid portions from a subset of foaming swine manure pits (data not shown). However, the ratio of methanogens relative to total prokaryotes in samples obtained from foaming deep pit swine manure storage systems was greater (P<0.05) compared to samples from swine manure pits without foam (FIG. 1A). Furthermore, the methanogen population was more abundant (P=0.08) in the liquid portion of foaming swine manure pits compared to the foam present on the liquid manure surface. The greater quantity of methanogens present suggests that the microbial community has a greater potential to produce methane gas in foaming deep pit swine manure storage units.

Example 8

Differences in Nutrient Composition of Swine Manure Samples Between Sites Feeding a *Bacillus*-Based Direct-Fed Microbial (DFM) for Waste Treatment and Untreated Sites Manure samples from deep pit storage systems on swine production sites with and without in-feed supplementation with a *Bacillus*-based DFM were collected and the nutrient composition of these samples was assessed. The *Bacillus*-based DFM included a combination of three *Bacillus* strains, B. subtilis 27 (NRRL B-50105), B. licheniformis 842 (NRRL B-50516), and B. licheniformis 21 (NRRL B-50134). The strains were administered in the following amounts: 70% of the total CFUs for the *Bacillus* strains of B. licheniformis 842 (NRRL B-50516), 10% of the total CFUs for the *Bacillus* strains of B. subtilis 27 (NRRL B-50105), and 20% of the total CFUs for the *Bacillus* strains of B. licheniformis 21 (NRRL B-50134). These three strains were administered in the feed to provide a total of $1 \times 10^5$ cfu/g of feed. This dose was approximately 36% greater than the previous recommendation for these strains which was $7.35 \times 10^4$ cfu/g of feed.

Manure samples were obtained by sampling the entire depth of the manure storage pit with a 6'-long PVC sampling rod. Moisture was greater (P 0.05) in manure samples from sites supplemented with *Bacillus* compared to sites without supplementation (Table 5). Manure samples obtained from deep-pit storage systems on sites supplementing with *Bacillus* had greater (P<0.05) concentrations of crude protein and ammonia-nitrogen compared to manure samples from unsupplemented sites. Conversely, manure samples from deep pit storage systems at sites that supplemented with *Bacillus* had lower (P<0.05) concentrations of crude fat, acid detergent fiber, and neutral detergent fiber. These data demonstrate the beneficial effects of the *Bacillus*-based DFM on swine waste management, specifically its ability to decrease fat and fiber nutrients associated with manure solids. Furthermore, the greater concentration of protein and nitrogen in supplemented manure samples suggests the *Bacillus* DFM decreases the quantity of nitrogen volatilized as ammonia.

TABLE 5

Nutrient concentration of samples from deep pit manure storage systems with and without administration of a *Bacillus*-based direct-fed microbial in the diet.

| | Control | Bacillus | SEM | P = |
|---|---|---|---|---|
| Moisture | 91.28 | 93.96 | 0.349 | 0.0001 |
| Crude fat | 13.29 | 10.61 | 0.816 | 0.0176 |
| Crude protein | 49.50 | 67.62 | 2.061 | 0.0001 |
| Ammonia N | 5.29 | 7.90 | 0.263 | 0.0001 |
| ADF | 18.69 | 15.01 | 0.484 | 0.0001 |
| NDF | 39.01 | 31.77 | 1.511 | 0.0007 |
| ADFProtein | 3.16 | 3.02 | 0.100 | 0.3108 |

Example 9

Differences in Microbial Populations Between Manure Samples from Deep Pit Swine Manure Systems at Sites Feeding a *Bacillus*-Based Direct-Fed Microbial (DFM) for Waste Treatment and Untreated Sites Manure samples from deep pit storage systems with and without in-feed supplementation with a *Bacillus*-based DFM were collected at various sites from three production systems. The microbial communities of these samples were assessed by terminal restriction fragment length polymorphism (T-RFLP) analysis. The *Bacillus*-based DFM used in this example was the same as the DFM used in Example 8, and it was administered at the same rate, i.e., $1 \times 10^5$ cfu/g of feed.

The microbial communities of these samples were assessed by terminal restriction fragment length polymorphism (T-RFLP) analysis. Manure samples at each site were obtained by sampling the entire depth of the manure storage pit with a 6'-long PVC sampling rod. Supplementation to the feed of growing-finishing pigs with the *Bacillus* DFM enhanced (P<0.05) populations of specific microbial TRFs (U87.01, U95.29, U278.54, U544.40, H32.98, H307.00, H314.32, M275.76, M297.38, M299.43, and M412.07), some of which were putatively identified as *Actinobacteria, Alphaproteobacteria, Campylobacter/Bacillus*, and *Clostridia*; Table 6). Furthermore, some TRFs (U187.38 and M248.14) putatively identified as sulfate-reducing bacteria (*Desulfobacteria, Desulfotomaculum*) that were greater in swine manure pits experiencing foaming, were less prominent (P<0.05) at sites supplemented with the *Bacillus* DFM compared to those at sites that were not supplemented. The propensity of the *Bacillus* DFM to alter microbial communities in swine manure deep pit systems supports the practice of applying the *Bacillus* DFM to control microbial fermentation to benefit the changing nutrient profiles resulting from current industry feeding practices and to alleviate the foaming phenomenon.

TABLE 6

Microbial populations resulting from terminal restriction fragment length polymorphism analysis of swine deep manure storage pits with and without administration of a *Bacillus*-based direct-fed microbial in the diet.

| TRF | Binary | | | Quantitative | | | |
|---|---|---|---|---|---|---|---|
| 8F | Control | Bacillus | P-value | Control | Bacillus | P-value | Putative Identification |
| U27.02 | 0.000 | 0.230 | 0.0031 | 0.000 | 186.434 | 0.0090 | |
| U62.25 | 0.000 | 0.214 | 0.0005 | 0.000 | 205.929 | 0.0058 | Alpha, Beta, Delta-, & Gamma proteobacteria |
| U87.01 | 0.332 | 0.536 | 0.1057 | 756.135* | 2657.754* | 0.0135* | Actinobacteria, Alphaproteobacteria (*hyphomonas*) |
| U95.29 | 0.086* | 0.666* | 0.0001* | 81.667* | 1662.001* | 0.0001* | |
| U109.38 | 0.000 | 0.480 | 0.0001 | 0.000 | 498.594 | 0.0001 | |
| U116.51 | 0.000 | 0.156 | 0.0217 | 0.000 | 169.563 | 0.0632 | Gammaproteobacteria, Bacteroidetes, Peptococcaceae(SRB) |
| U122.93 | 0.000 | 0.230 | 0.0031 | 0.000 | 415.257 | 0.0047 | |
| U124.90 | 0.000 | 0.284 | 0.0010 | 0.000 | 393.493 | 0.0048 | |
| U160.58 | 0.021 | 0.534 | 0.0001 | 50.479 | 954.784 | 0.0047 | |
| U163.02 | 0.266 | 0.595 | 0.0126 | 422.12 | 1305.767 | 0.0332 | |
| U187.38 | 0.290 | 0.037 | 0.0001 | 750.462** | 22.667** | 0.0001** | Actinobacterium, Desulfotomaculum(SRB) |
| U192.96 | 0.976 | 0.794 | 0.0237 | 4667.587 | 1962.982 | 0.0001 | |
| U215.01 | 0.000 | 0.230 | 0.0031 | 0.000 | 181.135 | 0.0037 | |
| U236.43 | 0.000 | 0.278 | 0.0006 | 0.000 | 172.717 | 0.0103 | *Bacillus* [a few others] |
| U241.34 | 0.000 | 0.193 | 0.0089 | 0.000 | 364.447 | 0.0193 | |
| U243.67 | 0.000 | 0.230 | 0.0031 | 0.000* | 1748.75* | 0.0060* | |
| U245.84 | 0.000 | 0.230 | 0.0031 | 0.000* | 1271.704* | 0.0280* | |
| U247.62 | 0.000 | 0.230 | 0.0031 | 0.000 | 343.915 | 0.0051 | |
| U249.75 | 0.000 | 0.230 | 0.0031 | 0.000 | 151.722 | 0.0150 | |
| U271.01 | 0.110 | 0.527 | 0.0006 | 254.238 | 772.723 | 0.0831 | |
| U278.54 | 0.192* | 0.823* | 0.0001* | 167.346* | 2265.655* | 0.0002* | *Campylobacter, Bacillus* [neither a good match] |
| U289.62 | 0.328 | 0.642 | 0.0104 | 1668.843 | 1015.072 | 0.2789 | |
| U297.87 | 0.976 | 0.770 | 0.0134 | 6455.083* | 3709.717* | 0.0011* | |
| U302.48 | 0.089 | 0.456 | 0.0013 | 92.387 | 436.467 | 0.0095 | |
| U362.47 | 0.000 | 0.230 | 0.0031 | 0.000 | 106.955 | 0.0047 | |
| U390.27 | 0.000 | 0.230 | 0.0031 | 0.000 | 198.712 | 0.0067 | |
| U409.05 | 0.000 | 0.230 | 0.0031 | 0.000 | 205.698 | 0.0115 | |
| U456.02 | 0.884 | 0.709 | 0.1068 | 1798.4238 | 924.082 | 0.0005 | |

TABLE 6-continued

Microbial populations resulting from terminal restriction fragment length polymorphism analysis of swine deep manure storage pits with and without administration of a *Bacillus*-based direct-fed microbial in the diet.

| TRF | Binary | | | Quantitative | | | |
|---|---|---|---|---|---|---|---|
| 8F | Control | *Bacillus* | P-value | Control | *Bacillus* | P-value | Putative Identification |
| U484.06 | 0.673 | 0.382 | 0.0242 | 946.022 | 226.970 | 0.0001 | *Wolbachia* [?] |
| U525.69 | 0.196 | 0.486 | 0.0115 | 157.567 | 626.385 | 0.0186 | |
| U544.40 | 0.104* | 0.503* | 0.0008* | 416.021 | 580.768 | 0.6814 | |
| H22.69 | 0.268 | 0.571 | 0.0215 | 415.375 | 1012.314 | 0.0354 | |
| H30.43 | 0.000 | 0.230 | 0.0031 | 0.000 | 501.241 | 0.0324 | Delta and Epsilon proteobacteria |
| H32.98 | 0.086* | 0.497* | 0.0005* | 93.780 | 795.252 | 0.0009 | |
| H62.63 | 0.418 | 0.940 | 0.0001 | 629.452 | 1464.312 | 0.0025 | |
| H81.82 | 0.000 | 0.325 | 0.0001 | 0.000 | 256.389 | 0.0002 | Bacteroidetes, Clostridiaceae |
| H213.09 | 0.021 | 0.395 | 0.0001 | 13.375 | 227.390 | 0.0003 | [many] |
| H219.52 | 0.131 | 0.527 | 0.0014 | 250.491 | 828.751 | 0.0451 | |
| H223.34 | 0.660 | 1.000 | 0.0003 | 1375.001 | 2154.228 | 0.0433 | |
| H226.94 | 0.976 | 0.976 | 1.000 | 1982.482 | 1048.801 | 0.0001 | |
| H232.82 | 0.292 | 0.693 | 0.0002 | 399.704 | 649.478 | 0.0712 | *Geobacillus, bacillus* |
| H238.15 | 0.747 | 0.976 | 0.0092 | 1493.680 | 2026.515 | 0.1039 | |
| H255.87 | 0.848 | 0.605 | 0.0365 | 1937.474 | 350.347 | 0.0001 | Multiple gammaproteobacteria |
| H264.73 | 0.170 | 0.386 | 0.0399 | 214.220 | 296.556 | 0.630 | Multiple Bacteroidetes, *Desulfotomaculum* |
| H274.78 | 0.577 | 0.946 | 0.0003 | 1174.082 | 1750.476 | 0.0575 | Deltaproteobacteria, clostridiales, desulfobacteria |
| H297.49 | 0.224 | 0.807 | 0.0001 | 538.318 | 1782.577 | 0.0019 | |
| H300.91 | 0.958 | 1.000 | 0.3396 | 3016.947 | 2134.139 | 0.0023 | Clostridia |
| H307.00 | 0.000* | 0.582* | 0.0001* | 0.000 | 512.634 | 0.0001 | |
| H314.32 | 0.089* | 0.801* | 0.0001* | 181.580* | 1305.170* | 0.0007* | |
| H320.58 | 0.688 | 0.898 | 0.0534 | 909.874 | 2040.329 | 0.0048 | |
| H325.45 | 0.000 | 0.362 | 0.0001 | 0.000 | 861.889 | 0.0005 | Gammaproteobacteria, *Lactobacillus* |
| H327.14 | 0.000 | 0.302 | 0.0002 | 0.000 | 252.521 | 0.0032 | |
| H618.46 | 0.128 | 0.432 | 0.0098 | 133.313 | 340.764 | 0.0600 | |
| H777.49 | 0.176 | 0.523 | 0.0057 | 209.030 | 565.324 | 0.0250 | |
| H804.90 | 0.063 | 0.464 | 0.0002 | 65.708 | 442.679 | 0.0022 | Desulfobacteraceae, deltaproteobacteria |
| M62.64 | 0.045 | 0.312 | 0.0018 | 42.307 | 215.966 | 0.0140 | *Bacillus, Geobacillus* |
| M87.18 | 0.000 | 0.156 | 0.0217 | 0.000 | 408.183 | 0.3512 | |
| M95.63 | 0.956 | 0.926 | 0.6286 | 6794.341 | 3516.423 | 0.0013 | |
| M106.66 | 0.152 | 0.527 | 0.0027 | 235.313 | 812.121 | 0.0920 | |
| M116.08 | 0.158 | 0.685 | 0.0001 | 199.280 | 756.687 | 0.0024 | |
| M124.72 | 0.577 | 0.348 | 0.0626 | 1926.017 | 703.984 | 0.0003 | *Halomonas*, actinobacteria, alpha and delta proteobacteria |
| M165.13 | 0.000 | 0.251 | 0.0003 | 0.000 | 238.513 | 0.0103 | *Bacillus*, Desufobacteria, deltaproteobacteria |
| M192.84 | 0.000 | 0.254 | 0.0015 | 0.000 | 622.693 | 0.0052 | |
| M198.90 | 0.000 | 0.217 | 0.0042 | 0.000 | 171.452 | 0.0272 | *Halomonas*, Clostridia, Acidobacteria |
| M208.09 | 0.063 | 0.254 | 0.0410 | 55.938 | 267.579 | 0.0341 | |
| M209.56 | 0.042 | 0.328 | 0.0045 | 60.521 | 602.915 | 0.0106 | |
| M224.81 | 0.618 | 0.929 | 0.0027 | 1134.734 | 2453.932 | 0.0098 | |
| M232.96 | 0.152 | 0.540 | 0.0019 | 161.598 | 496.955 | 0.0150 | |
| M243.82 | 0.955 | 0.770 | 0.0371 | 10069.902** | 4480.534** | 0.0001** | |
| M248.14 | 0.756 | 0.709 | 0.7022 | 2349.089** | 1224.732** | 0.0082** | Desulfobacteria |
| M275.76 | 0.726 | 0.909 | 0.0698 | 1293.253* | 4018.015* | 0.0001* | |
| M281.76 | 0.000 | 0.230 | 0.0031 | 0.000 | 139.672 | 0.0035 | |
| M291.85 | 0.000 | 0.230 | 0.0031 | 0.000 | 520.116 | 0.0782 | |
| M297.38 | 0.000 | 0.230 | 0.0031 | 0.000* | 1227.021* | 0.0130* | |
| M299.43 | 0.000 | 0.412 | 0.0001 | 0.000* | 968.40* | 0.0359* | |
| M301.05 | 0.000 | 0.206 | 0.0057 | 0.000 | 330.894 | 0.0499 | |
| M380.69 | 0.171 | 0.581 | 0.0007 | 117.417 | 373.955 | 0.0054 | |
| M387.90 | 0.089 | 0.497 | 0.0006 | 149.929 | 638.105 | 0.0138 | |
| M401.59 | 0.217 | 0.581 | 0.0044 | 347.417 | 653.346 | 0.4001 | |
| M408.58 | 0.352 | 0.648 | 0.0241 | 585.992 | 591.708 | 0.9772 | |
| M412.07 | 0.107* | 0.612* | 0.0001* | 126.107 | 384.608 | 0.0133 | |
| M458.92 | 0.000 | 0.206 | 0.0057 | 0.000 | 311.616 | 0.0100 | |
| M507.30 | 0.000 | 0.254 | 0.0015 | 0.000 | 279.040 | 0.0392 | |
| M517.73 | 0.000 | 0.230 | 0.0031 | 0.000 | 501.709 | 0.0209 | |
| M525.11 | 0.021 | 0.397 | 0.0001 | 12.958 | 537.593 | 0.0035 | |
| M536.48 | 0.000 | 0.230 | 0.0031 | 0.000 | 319.712 | 0.0049 | |
| M542.74 | 0.000 | 0.230 | 0.0031 | 0.000 | 198.981 | 0.0101 | Bacteroidetes |
| M559.14 | 0.000 | 0.230 | 0.0031 | 0.000 | 242.40 | 0.0375 | |

*indicates values are distinctly greater in samples from *Bacillus*-based DFM treated pits compared to non-treated pits.
**indicates values are distinctly greater in samples from non-treated pits compared to *Bacillus*-based DFM treated pits

Example 10

Quantitative Analysis of Sulfate-Reducing Bacteria and Methanogens in Manure Samples from Deep Pit Swine Manure Storage Systems at Sites Feeding a Bacillus-Based Direct-Fed Microbial for Waste Treatment and Untreated Sites To assess the potential of the *Bacillus*-based DFM to alter microbial communities in swine manure deep pit storage systems with foam, quantities of sulfate-reducing bacteria and methanogens were determined in manure samples from sites supplemented with a *Bacillus* DFM in the feed compared to untreated sites. The *Bacillus*-based DFM used in this example was the same as the DFM used in Example 8, and it was administered at the same rate, i.e., $1 \times 10^5$ cfu/g of feed.

Figure 2A:
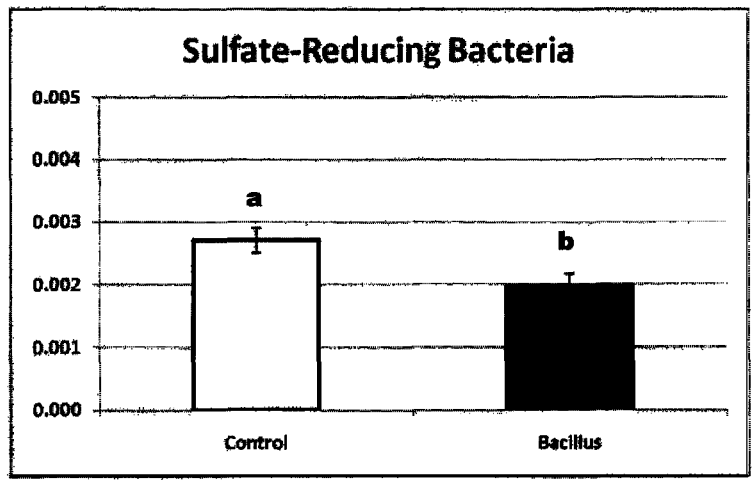
FIGS. 2A-2B are graphs showing quantity of sulfate-reducing bacteria (FIG. 2A) and methanogens (FIG. 2B) in samples from swine deep-pit manure storage systems with and without supplementation with a *Bacillus*-based direct-fed microbial in the feed of grow-finish pigs. Data are expressed as a ratio of sulfate-reducing bacterial or methanogen DNA relative to total prokaryote DNA in each sample as measured by delta Ct values analyzed by quantitative real-time PCR. [a,b] Means without similar letters are significantly different (P<0.05).
Figure 2B:
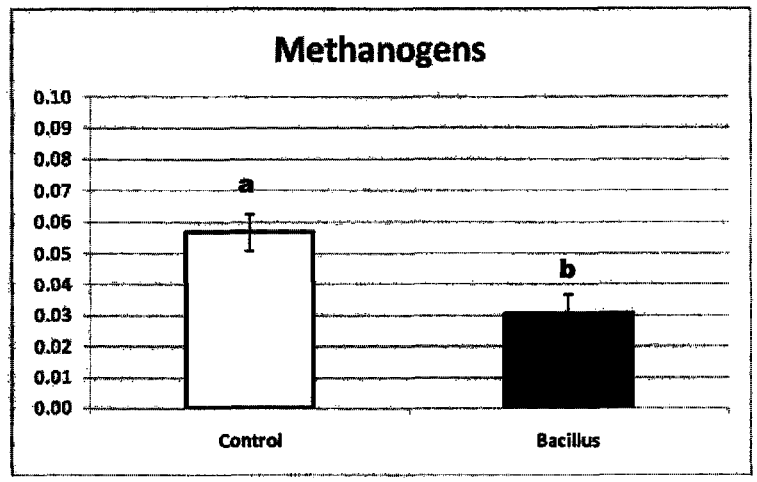

The ratio of sulfate-reducing bacteria and methanogens relative to total prokaryotes in samples obtained from deep pit swine manure storage systems at sites supplemented with *Bacillus* was lower (P<0.05) compared to samples from swine manure pits from untreated sites (FIGS. 2A-2B). These data demonstrate the ability of the *Bacillus* DFM to alter microbial populations indicative of effective anaerobic digestion, in response to current swine industry feeding practices and their manure nutritive consequences.

Example 11

Use of Dried Distiller's Grains with Solubles (DDGS) in Commercial Swine Production, Use of a Bacillus-Based Microbial Treatment, and Incidence of Foaming in Deep Pit Manure Systems Three commercial swine producers, Producers A, B, and C, were surveyed about the incidence of foaming in their deep pit swine manure storage systems, their use of a direct-fed microbial *Bacillus* to address swine waste management issues, and their nutrition program, specifically related to the level of DDGS in the diet. All producers used the *Bacillus*-based DFM described in Example 8.

In this example, that is, Example 11, "recommended dose" refers to the dose recommended for using the *Bacillus*-based DFM for improve the decomposition of stored swine manure, which is a previous use for this *Bacillus*-based DFM. See, e.g., footnote 2 of Table 7. This recommended dose is $7.35 \times 10^4$ CFU/g of feed. Table 7 provides a summary of the producer survey results.

TABLE 7

Summary of the number and percentage of swine deep-pit manure units experiencing foaming from a survey of three producers (A, B, and C), relative to inclusion level of the manure treatment *Bacillus*-based DFM.

| Producer | A | B | C | |
|---|---|---|---|---|
| Year | | | Time Pt. A | 2 years later |
| Number of pits assessed | 64 | 60 | 400 | 400 |
| DDGS %[1] | 8 | 18 | 15 | 15 |
| *Bacillus* DFM inclusion, %[2] | 92 | 108 | 118 | 0 |
| *Bacillus* DFM inclusion, cfu/g of feed | $6.8 \times 10^4$ | $7.9 \times 10^4$ | $8.7 \times 10^4$ | 0 |
| Relative *Bacillus* DFM inclusion, %[3] | 80 | 98 | 104 | 0 |
| Non-foaming pits, n | 60 | 60 | 400 | 60 |
| Foaming pits, n | 4 | 0 | 0 | 340 |
| Foaming pits, % | 6.25 | 0 | 0 | 85 |

[1]Percentage of dried distiller's grains with solubles (DDGS) included in each producer's diet formulation for growing-finishing pigs.
[2]Average percentage of the waste treatment *Bacillus*-based DFM fed relative to the recommended dose per ton of feed ($7.35 \times 10^4$ cfu/g of feed) accounting for the decreased inclusion level of the premix over the growing-finishing period or additional DFM added over the recommended level. Decreased dosages were the result of reduced VTM inclusion in phase 4-6 of finishing diets.
[3]Average percentage of the waste treatment *Bacillus*-based DFM fed relative to the actual nitrogen content of manure. Manure nitrogen content increased with the inclusion of DDGS compared to what would be expected when feeding a typical corn-soybean meal based diet.

Sixty-four deep pit units were assessed from Producer A, who was feeding 8% DDGS in the growing-finishing diets. Producer A incorporated a step-down program in which the level of vitamin-trace mineral premix including the *Bacillus* DFM was decreased with each feeding phase in the grow-finish period, thereby resulting in the DFM being included at $6.8 \times 10^4$ cfu/g of feed on average over the course of the grow-finish period. This inclusion rate was 92% of the recommended level of $7.35 \times 10^4$ cfu/g of feed that was previously used to improve decomposition of stored swine manure. When accounting for the increase in nitrogen excretion by pigs fed diets containing 8% DDGS, Producer A was feeding only 80% of the recommended dose of the DFM relative to the nitrogen content of the manure. Producer A experienced foaming in approximately 6% of deep pit manure holding units in the 64 pits assessed. Thus, it can be seen that feeding too little *Bacillus*-based DFM does not control foaming in manure pits.

In contrast to Producer A, Producer B was feeding 18% DDGS in the diets and the waste treatment DFM at $7.9 \times 10^4$ cfu/g of feed, greater than the recommended level of $7.35 \times 10^4$ cfu/g of feed. Producer B fed 108% of the recommended level on average over the grow-finish period when incorporating a similar step-down program with the vitamin-trace mineral premix as Producer A, and was still very close to the recommended level of the DFM relative to the increase in manure nitrogen content resulting from the 18% DDGS incorporation. Of the 60 deep pit manure systems assessed in Producer B's system, none of the pits experienced any incidences of foaming. This example shows that feeding increased amounts over the recommended dose of the *Bacillus*-based DFM for improving decomposition of stored swine manure controls foaming in manure pits.

Producer C provides unique insight into the potential of the *Bacillus* DFM to control the decomposition of nutrients present in swine deep pit manure storage systems to enhance anaerobic decomposition. At one time point, Producer C was feeding 15% DDGS in grow-finish and was feeding the *Bacillus* DFM at greater than the recommended level, even when accounting for the greater manure nitrogen associated with the DDGS inclusion level. Producer C was feeding the *Bacillus* DFM at $8.7 \times 10^4$ cfu/g of feed, greater than the recommended level of $7.35 \times 10^4$ cfu/g of feed, even when accounting for the greater manure nitrogen associated with the DDGS inclusion level. Of the 400 deep pit units assessed within Producer C's system, none had experienced foaming. Producer C then removed the Bacillus DFM from grow-finish diets. For the next two years, the inclusion of DDGS remained at 15% and in some cases greater. After two years of not including the Bacillus DFM in grow-finish diets, Producer C was experiencing foaming in 85% of the deep pit units (340 of the 400 deep pit manure storage units assessed were foaming).

The presence of several TRFs putatively identified as Bacillus species were present in both foaming and non-foaming deep pit swine manure storage facilities (Table 8), illustrating that native Bacillus organisms are present in the environment and have no effect on the incidence of foaming in deep pit swine manure storage systems. These data also demonstrate that the selected Bacillus strains in the DFM administered in these examples alter the microbial ecology of the swine manure pit and decrease the incidence of foam distinctly from other Bacillus bacteria.

TABLE 8

Terminal restriction fragments (TRFs) in high and low foaming and non-foaming swine manure pits that were putatively identified as Bacillus species.

| | Binary | | | | Quantitative | | | | Putative |
| --- | --- | --- | --- | --- | --- | --- | --- | --- | --- |
| TRF | High | Low | None | P-value | High | Low | None | P-value | Identification |
| U95.29 | 0.33 | 0.31 | 0.49 | 0.2405 | 983.61 | 513.57 | 1118.32 | 0.2347 | Bacillus sp. |
| U148.60 | 0.06 | 0.00 | 0.04 | 0.5901 | 37.61 | 0.00 | 11.11 | 0.4717 | Bacillus sp. |
| U160.58 | 0.33 | 0.18 | 0.32 | 0.3417 | 840.39 | 127.09 | 540.36 | 0.1918 | Bacillus litoralis |
| U223.47 | 0.38 | 0.54 | 0.38 | 0.4207 | 450.01 | 1533.48 | 1496.85 | 0.4080 | Bacillus cibi |
| H32.98 | 0.22 | 0.31 | 0.34 | 0.7033 | 187.17 | 462.68 | 683.71 | 0.1586 | Bacillus sp. |
| H179.21 | 0.06 | 0.00 | 0.04 | 0.5901 | 17.56 | 0.00 | 14.96 | 0.6136 | Bacillus subtilis subsp. subtilis |
| H223.34 | 0.90 | 0.71 | 0.88 | 0.1505 | 1610.86 | 1496.61 | 2186.38 | 0.1930 | Bacillus edaphicus |
| H279.66 | 0.90 | 0.66 | 0.77 | 0.2543 | 1663.08 | 897.81 | 1247.44 | 0.2413 | Bacillus niacin & flexus |
| H289.49 | 1.00 | 0.96 | 0.96 | 0.7991 | 2065.69 | 2345.60 | 2508.13 | 0.6381 | Bacillus sp. |
| H297.49 | 0.60 | 0.46 | 0.49 | 0.6146 | 1526.03 | 1128.03 | 827.28 | 0.3605 | Bacillus funiculus |
| H307.00 | 0.33 | 0.18 | 0.36 | 0.1577 | 316.56 | 198.18 | 254.21 | 0.7057 | Bacillus licheniformis, subtilis subsp. Subtilis, & sp. |
| H314.32 | 0.50 | 0.34 | 0.49 | 0.2550 | 1079.83 | 573.35 | 576.94 | 0.4111 | Bacillus tipchiralis & sp. |
| M32.61 | 0.00 | 0.04 | 0.03 | 0.8201 | 0.00 | 351.89 | 279.28 | 0.8136 | Bacillus solfatarensis |
| M148.87 | 0.06 | 0.00 | 0.11 | 0.2299 | 20.83 | 0.00 | 77.54 | 0.2526 | Bacillus sp. |
| M216.15 | 0.90 | 0.77 | 0.86 | 0.4985 | 990.60 | 1375.01 | 1164.97 | 0.5961 | Bacillus flexus |
| M401.59 | 0.22 | 0.47 | 0.50 | 0.1931 | 101.38 | 555.52 | 844.23 | 0.2795 | Bacillus sp. |
| M458.92 | 0.17 | 0.00 | 0.14 | 0.1072 | 252.39 | 0.00 | 215.05 | 0.1452 | Bacillus sp. |
| M486.74 | 0.17 | 0.00 | 0.14 | 0.1072 | 85.94 | 0.00 | 74.00 | 0.1290 | Bacillus sp. |

The results from Producers A-C indicate a strong link between nutrient input into the anaerobic decomposition system of deep pit swine manure storage systems and guiding the decomposition of organic matter from swine manure by specific Bacillus strains in the Bacillus-based DFM. Examples 1 and 2 demonstrate the increased nitrogen excreted in the feces of pigs fed DDGS and the corresponding increase in nitrogen in manure storage pits. Foaming is associated with nutrient overloading surpassing the capacity of the anaerobic decomposition process. Therefore, specific strains of microorganisms with the ability to shift the microbial milieu within deep pit swine manure systems to support anaerobic decomposition are an important technology for managing swine manure decomposition and foaming phenomenon.

Example 12

Microbial Populations Putatively Identified as Bacillus Species Present in Foaming and Non-Foaming Swine Deep Pit Manure Systems Manure samples from deep pit storage systems with and without foam were collected at various sites from three production systems that were feeding the Bacillus-based DFM described in Example 8, and it was administered at the same rate described in Example 8, i.e., $1 \times 10^5$ cfu/g of feed.

The microbial communities of these samples were assessed by T-RFLP analysis. Manure samples at each site were obtained and classified as in Example 2.

Example 13

Use of Bacillus subtilis Strain LSSAO1 to Control Foaming in Deep Pit Swine Manure Storage Systems Through Direct Application of the Bacterial Additive to the Manure System Foaming was assessed in deep pit swine manure storage systems displaying foaming at four production sites in which the foam portion of the total manure depth in the pit ranged from 21.43% to 62.50% (Table 9). Two foaming manure pits were identified at each site. Bacillus subtilis strain LSSAO1 was administered directly to one of the manure pits at each site and the other manure pit was left untreated to compare the proportion of foam relative to the total manure depth between control and treated manure pits. The dose of LSSAO1 averaged $6.4 \times 10^4$ cfu/mL of manure volume in each treated pit. Administration of LSSAO1 decreased the percentage of foam relative to the total manure depth to a greater extent than when the manure pits were not treated with LSSAO1. Notably, LSSAO1 completely eliminated foam at two of the sites (F024 and F080) 40 days after inoculation of the strain into foaming manure pits. A summary of the data from the four sites indicates the percentage of foam decreased from 39.73% to 4.69% after treatment with LSSAO1, whereas foam decreased to a lesser extent (27.23% to 18.54%) in pits left untreated. These data indicate the microbial activity of LSSAO1 was efficacious in alleviating the foaming conditions observed in deep pit swine manure storage systems.

TABLE 9

Effect of the administration of *Bacillus subtilis* strain LSSAO1 relative to the percentage of foam as part of the total manure pit volume prior to and 40 days after direct application into foaming deep pit swine manure systems at four production sites.

| Site # | Treatment | Trt Level (1,000 cfu/ml) | Day 0 Total (ft) | Day 0 Foam (ft) | Day 0 % Foam | Day 40 Total (ft) | Day 40 Foam (ft) | Day 40 % Foam |
|---|---|---|---|---|---|---|---|---|
| F024 | LSSAO1 | 76 | 5.00 | 2.50 | 50.00 | 3.00 | 0.00 | 0.00 |
|  | Control | 0 | 4.00 | 1.50 | 37.50 | 2.50 | 0.50 | 20.00 |
| F025 | LSSAO1 | 64 | 3.50 | 0.75 | 21.43 | 2.00 | 0.25 | 12.50 |
|  | Control | 0 | 3.50 | 0.75 | 21.43 | 2.00 | 0.50 | 25.00 |
| F080 | LSSAO1 | 71 | 3.00 | 0.75 | 25.00 | 2.00 | 0.00 | 0.00 |
|  | Control | 0 | 3.00 | 0.75 | 25.00 | 2.00 | 0.25 | 12.50 |
| F249 | LSSAO1 | 44 | 4.00 | 2.50 | 62.50 | 4.00 | 0.25 | 6.25 |
|  | Control | 0 | 4.00 | 1.00 | 25.00 | 3.00 | 0.50 | 16.67 |
| Treatment Summary | | | | | | | | |
|  | LSSAO1 | Mean | 3.88 | 1.63 | 39.73 | 3.75 | 0.13 | 4.69 |
|  | Control | Mean | 3.63 | 1.00 | 27.23 | 2.38 | 0.44 | 18.54 |

Example 14

Overview Over Sampled Farms and Establishment of a Prediction System Comparing *Bacillus* Direct-Fed Microbial Application in Deep Swine Manure Pit Systems Complete depth-manure samples from 217 randomly selected deep pit storage systems on swine production sites with (n=141) and without (n=76) in-feed supplementation with a *Bacillus*-based DFM were collected. The *Bacillus*-based DFM was added to feed at a rate of $8.8 \times 10^4$ total CFU of all strains/g of feed. Ad libitum access to feed was available to all pigs throughout each production cycle at each production site. The *Bacillus*-based DFM included a combination of three strains, *B. subtilis* 27 (NRRL B-50105), B. licheniformis 842 (NRRL B-50516), and *B. licheniformis* 21 (NRRL B-50134). The strains were administered in the following amounts: 70% of the total CFUs for the *Bacillus* strains were B. licheniformis 842 (NRRL B-50516), 10% of the total CFUs for the *Bacillus* strains were *B. subtilis* 27 (NRRL B-50105), and 20% of the total CFUs for the *Bacillus* strains were *B. licheniformis* 21 (NRRL B-50134). Manure samples were obtained by sampling the entire depth of the manure storage pit with a 6'-long PVC sampling rod. Foam height was distinguished within three foaming categories: None=less than 2.0 inches of foam on the manure surface, low=3.0 to 15.0 inches of foam on the manure surface, and high=greater than 15.0 inches of foam on the manure surface.

The factors foam height, manure height and manure dry matter were assessed. To prove the connection between foam height, manure height and dry matter of pits sampled, correlation analysis was performed using correlate bivariate and partial correlate functions with pearson option of SPSS17.0 statistical software. Partial correlation allowed for detection of correlations which are overlaid by other factors. Here, statistical analysis was performed either independent or uncontrolled for *Bacillus* DFM treatment versus partial correlation analysis controlled for *Bacillus* DFM treatment. Curve estimation regression function of SPSS17.0 statistical software was used and linear, quadratic and cubic prediction scenarios were tested.

The number of production sites with foaming deep manure pits in the highest foaming category was about 2.5 fold increased compared between sites with *Bacillus* DFM treatment vs. untreated (9.4% vs. 22.4%, respectively; Table 10). The maximal foam height measured was almost double in untreated pits (48 inches vs. 84 inches, respectively). Correlation analysis between manure height and foam height, as well as between manure height and dry matter was highly significant (P<0.001; Tables 11, 12). In the uncontrolled correlation analysis, DM was not correlated with foam height (P=0.29) which changed to a significant correlation (P<0.01) if analysis performed was controlled for *Bacillus* DFM treatment. This supports a significant effect of *Bacillus* DFM on dry matter content in swine manure pits.

TABLE 10

Overview over 214 randomly picked GF barn pits in the US Midwest.

| Probiotic application | untreated pits | | | treated pits | | |
|---|---|---|---|---|---|---|
| Foaming category | 0 | 1 | 2 | 0 | 1 | 2 |
| Observed foam height range | 0-2 in | 3-12 in | 18-84 in | 0-2 in | 3-12 in | 16-48 in |
| Observed manure depth range | 2-4 ft | 2-7 ft | 3-7 ft | 2-7 ft | 2-7 ft | 4-8 ft |
| Sites absolute[1] | 22 | 37 | 17 | 49 | 76 | 13 |
| Sites relative | 28.9% | 48.7% | 22.4% | 35.5% | 55.1% | 9.4% |

[1] 76 untreated sites vs. 138 sites treated with *Bacillus* direct-fed microbial.

TABLE 11

Correlation analysis of foam height, manure height and dry matter not controlled for *Bacillus* DFM treatment.

| | | Foam height | Manure height | Dry matter |
|---|---|---|---|---|
| Foam height | Pearson correlation | 1 | 0.400 | −0.068 |
| | Significance | — | <.001 | 0.285 |
| Manure height | Pearson correlation | 0.400 | 1 | −0.454 |
| | Significance | <.001 | — | <.001 |
| Dry matter | Pearson correlation | −0.068 | −0.454 | 1 |
| | Significance | 0.285 | <.001 | — |

Comments: Two-tailed test of significance, significance level α = 0.050.

TABLE 12

Correlation analysis of foam height, manure height and dry matter not controlled for *Bacillus* DFM treatment.

| | | Foam height | Manure height | Dry matter |
|---|---|---|---|---|
| Foam height | Pearson correlation | 1 | 0.436 | −0.177 |
| | Significance | — | <.001 | 0.005 |
| Manure height | Pearson correlation | 0.436 | 1 | −0.402 |
| | Significance | <.001 | — | <.001 |
| Dry matter | Pearson correlation | −0.177 | −0.402 | 1 |
| | Significance | 0.005 | <.001 | — |

Comments: Two-tailed test of significance, significance level α = 0.050.

Figure 3:
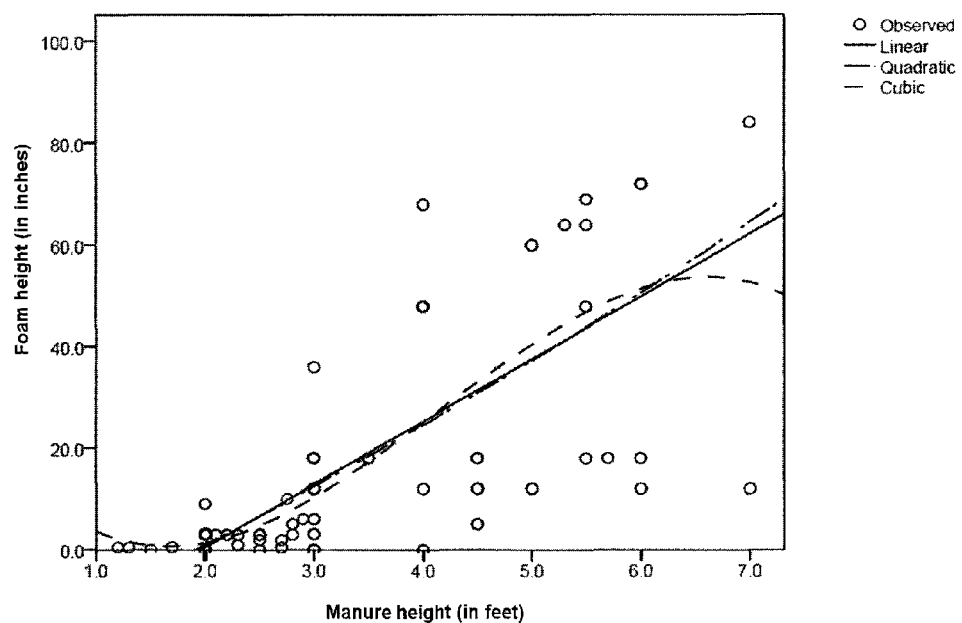
FIG. 3 is a graph showing curve prediction of foam height at sites with untreated manure pits depending on manure height.
Figure 4:
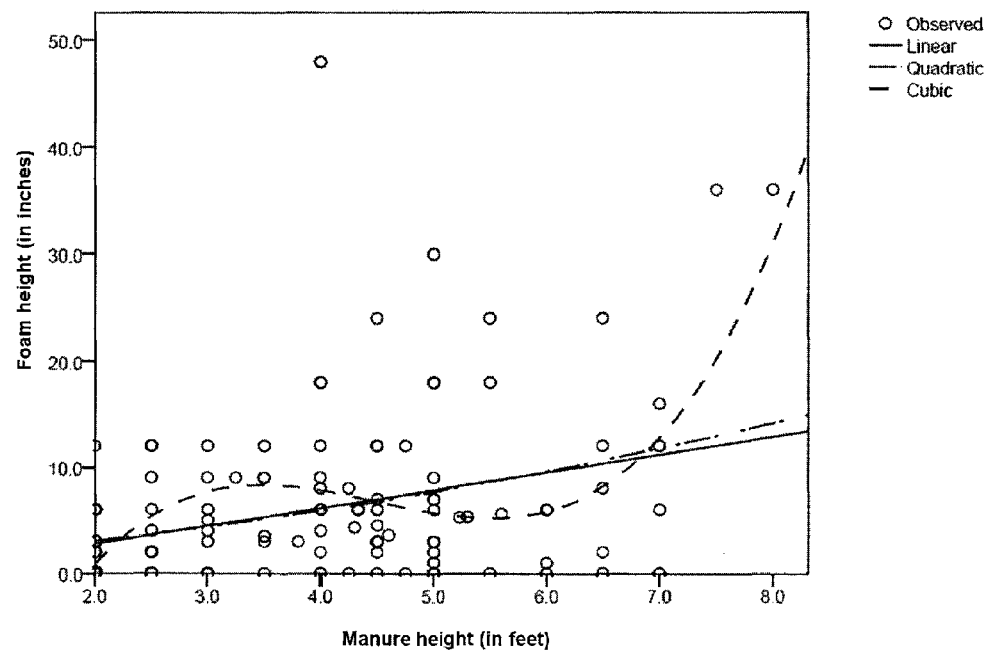
FIG. 4 is a graph showing curve prediction of foam height at sites with *Bacillus* treated manure pits depending on manure height.

Regression analysis was performed to predict foam height by manure height in deep pit swine manure storage facilities. Analysis was performed separately for *Bacillus* DFM treated and untreated production sites and is valid for ranges from 2-7 ft manure height for untreated sites and 2-8 ft for sites with *Bacillus* DFM treated pits. The regression was highly significant for all scenarios (P<0.001), thus the $R^2$ value indicating accuracy of prediction was used to select the best fit. Cubic prediction parameters were the best fitting scenarios in both untreated (P<0.001, $R^2$=0.55; see Table 13) and treated pits (P<0.001, $R^2$=0.20; see Table 14). Foam height values in untreated pits had a steady increase in predicted foam height of approximately 10 inches (0-40 inch measured range) at 3 ft manure height to approx. 50 inches (10-84 inch measured range) at 7 ft manure height (see FIG. 3). Differing from these findings, the predicted foam height in *Bacillus* treated pits increases from 8 inches to 10 inches only between 3 ft and 7 ft manure height (0-30 inch measured range+one site at 48 inch; see FIG. 4). After this initial lag phase in the *Bacillus* treated pits, the predicted foam height drastically increases to approx. 35 inch at 8 ft of manure height, which is still lower than the predicted 50 inch of foam at 7 ft of manure in untreated pits.

TABLE 13

Curve prediction model summary and parameter estimates for sites without *Bacillus* DFM treatment.

| Equation | Model summary | | Parameter estimates | | | |
|---|---|---|---|---|---|---|
| | Sign. | $R^2$ | Constant | b1 | b2 | b3 |
| Linear | <.001 | 0.531 | −24.228 | 12.358 | 0 | 0 |
| Quadratic | <.001 | 0.532 | −19.977 | 9.844 | 0.321 | 0 |
| Cubic | <.001 | 0.546 | 22.335 | −28.512 | 10.768 | −0.868 |

Comments: Significance level α = 0.050; Sign. = Significance; Independent variable X is manure height (in feet), dependent variable Y = foam height (in inch); Model: Y = constant + b1 * X + b2 * $X^2$ + b3 * $X^3$; Prediction valid from 1.5 ft to 7.0 ft manure height in untreated pits.

TABLE 14

Curve prediction model summary and parameter estimates for sites with *Bacillus* DFM treatment.

| Equation | Model summary | | Parameter estimates | | | |
|---|---|---|---|---|---|---|
| | Sign. | $R^2$ | Constant | b1 | b2 | b3 |
| Linear | <.001 | 0.092 | −0.578 | 1.679 | 0 | 0 |
| Quadratic | <.001 | 0.093 | 1.114 | 0.764 | 0.108 | 0 |
| Cubic | <.001 | 0.195 | −51.234 | 43.293 | −10.140 | 0.752 |

Comments: Significance level α = 0.050; Sign. = Significance; Independent variable X is manure height (in feet), dependent variable Y = foam height (in inch); Model: Y = constant + b1 * X + b2 * $X^2$ + b3 * $X^3$; Prediction valid from 2.0 ft to 8.0 ft manure height in *Bacillus* DFM treated pits.

Example 15

Differences in Manure Characteristics and in Quantities of Methanogens and Sulfate-Reducing Bacteria Associated with Probiotic *Bacillus* DFM Treatment Manure samples from 217 randomly selected deep pit storage systems on swine production sites with (n=141) and without (n=76) in-feed supplementation with a *Bacillus*-based DFM were collected and manure characteristics assessed. Quantities of methanogens and sulfate-reducing bacteria relative to total prokaryotes counts were determined by qPCR. The *Bacillus*-based DFM used in this example was the same as in Example 14. Manure samples were obtained by sampling the entire depth of the manure storage pit with a 6'-long PVC sampling rod. Data was normalized for a manure height of 3.75 ft for statistical analysis.

Addition of the *Bacillus*-based DFM was associated with reduced foam height, reduced dry matter content and viscosity (P≤0.001) in swine manure pits (Table 15). Manure pH was not affected by treatment. Methanogen counts were 1.3 fold increased (P<0.05), indicating stabilized anaerobic fermentation in *Bacillus* DFM treated pits. Sulfate-reducing bacteria were highly significantly decreased (P<0.001) to one third of their amount in untreated pits due to *Bacillus* DFM treatment. It is likely that the higher amount of sulfur detected in treated manure pits (P<0.05) was connected to these findings, indicating that more sulfur was bound in the aqueous phase of the pit as sulfate and did not emit as hydrogen sulfide into the barn environment (Table 16). The amounts of sodium, iron and zinc were increased in *Bacillus* DFM treated pits (P≤0.001), and the amount of copper was reduced (P=0.001) compared with untreated swine manure pits.

TABLE 15

Comparison of untreated vs. *Bacillus* treated swine pit physical characteristics and methanogenic archea and sulfur reducing bacteria quantities.

|  | Fheight | DM | pH | Visc | MA | SRB |
|---|---|---|---|---|---|---|
| Untreated | 10.766 | 8.546 | 7.785 | 399.980 | 0.0054 | 0.0344 |
| Treated | 6.492 | 6.567 | 7.778 | 213.705 | 0.0073 | 0.0128 |
| Significance | <.001 | 0.001 | 0.071 | <.001 | 0.002 | <.001 |
| SEM | 0.816 | 0.157 | 0.013 | 13.533 | 0.0006 | 0.0023 |

Comments: Analysis normalized to 3.75 ft manure height, significance level α = 0.05.
Fheight = foam height (in inch), DM = dry matter (in %), Visc = viscosity (in cps), MA = methanogenic archea, SRB = sulfur reducing bacteria. Archea and bacteria in fold changes relative to prokaryote quantity.

TABLE 16

Mineral composition differences in untreated vs. *Bacillus* treated swine pits.

|  | Ash | Ca | K | Mg | Na | P | S | Al | Cu | Fe | Mn | Zn |
|---|---|---|---|---|---|---|---|---|---|---|---|---|
| Untreated | 20.415 | 2.069 | 4.333 | 1.251 | 1.026 | 1.933 | 0.994 | 0.6080 | .406 | 1.5920 | .367 | 1.216 |
| Treated | 21.771 | 2.028 | 4.959 | 1.318 | 1.365 | 2.113 | 1.134 | 0.5000 | .360 | 2.2070 | .369 | 1.785 |
| Significance | 0.383 | 0.269 | 0.680 | 0.193 | 0.001 | 0.260 | 0.036 | 0.264 | 0.001 | <.001 | 0.651 | <.001 |
| SEM | 0.275 | 0.0420 | .088 | 0.0210 | .026 | 0.036 | 0.016 | 0.0360 | .010 | 0.0490 | .006 | 0.059 |

Comments: Analysis normalized to 3.75 ft manure height, significance level α = 0.05.
All data in % of total sample.

A high abundance of easily fermentable carbohydrates, here determined as nitrogen free extract (NfE), are responsible for bacterial overgrowth, for example in cattle's rumen. The highly significant reduction ($P<0.001$) of NfE by *Bacillus* DFM treatment stabilized the bacterial community in the swine manure pit (Table 17). Overall nitrogen secretion of swine fed *Bacillus* treatment was not significantly affected. More nitrogen was bound as ammonium in the aqueous phase of the manure ($P<0.001$), and thus not emitted in the form of flammable ammonia gas into the barn environment when treated with *Bacillus* DFM. Numerically, more nitrogen was bound to acid detergent fiber. The amount of acid and neutral detergent fiber was reduced in *Bacillus* DFM treated manure pits ($P\leq0.001$) compared with untreated pits.

The fat and volatile fatty acid content was not affected by treatment (Table 18), except for an increase of iso-butyrate in *Bacillus* DFM treated pits ($P<0.05$).

TABLE 17

Comparison of untreated vs. *Bacillus* treated swine pits in nitrogen distribution and fibre characteristics.

|  |  | Nitrogen | | | Fiber | | |
|---|---|---|---|---|---|---|---|
|  | NfE[1] | total N | NH4_N | ADF_N | ADF | NDF | CF |
| Untreated pits | 6.960 | 7.636 | 5.806 | 0.563 | 17.938 | 39.700 | 12.644 |
| Treated pits | 2.838 | 8.800 | 8.189 | 0.753 | 15.811 | 33.644 | 11.262 |
| Significance | <.001 | 0.430 | <.001 | 0.106 | <.001 | 0.001 | 0.123 |
| SEM | 0.390 | 0.358 | 0.158 | 0.039 | 0.199 | 0.588 | 0.218 |

[1]Calculated value, NfE = 100 − (crude protein + ether extract + crude fiber + ash), fraction contains mostly starches and sugars.
Comments: Analysis normalized to 3.75 ft manure height, significance level α = 0.05.
NfE = nitrogen free extract, N = nitrogen, NH4_N = aqueous ammonia bound nitrogen, ADF_N = acid detergent fiber bound nitrogen, ADF = acit detergent fibre, NDF = neutral detergent fiber, CF = crude fiber.
All data in percent of total sample.

TABLE 18

Fat and volatile fatty acid composition changes in untreated vs. *Bacillus* treated swine manure pits.

|  | EE | Tot vFA[1] | Acet | Prop | iButy | Buty | iVale |
|---|---|---|---|---|---|---|---|
| Untreated | 11.542 | 0.5013 | 0.3403 | 0.1441 | 0.0000 | 0.0015 | 0.0154 |
| Treated | 10.115 | 0.4210 | 0.2862 | 0.1106 | 0.0013 | 0.0010 | 0.0226 |
| Significance | 0.473 | 0.297 | 0.268 | 0.847 | 0.025 | 0.714 | 0.110 |
| SEM | 0.324 | 0.0283 | 0.0187 | 0.0101 | 0.0005 | 0.0008 | 0.0037 |

[1]Value calculated as sum of vFAs. Valearate analysed but below vFA detection level.
Comments: Analysis normalized to 3.75 ft manure height, significance level α = 0.05.
EE = crude fat or ether extract, Tot vFA = total volatile fatty acids, Acet = acetate, Prop = propionate, iButy = iso-butyrate, Buty = butyrate, iVale = iso-valerate.
All data in percent of total sample.

The overall reduction of organic matter, mostly shown in the reduction of NfE and fiber (P≤0.001; Table 17) but also in the numerical decrease in fat, reduced the nutrient load in the *Bacillus* treated pits, which stabilized anaerobic fermentation as indicated in the higher methanogen counts (Table 15) and the higher production of iso-butyrate (Table 18) due to more stable bacterial fermentation.

Example 16

Differences in Physical Manure Characteristics and in Quantities of Methanogens and Sulfate-Reducing Bacteria Associated with Probiotic *Bacillus* DFM Treatment and Degree of Pit Foaming Manure samples from 217 randomly selected deep pit storage systems on swine production sites with (n=141) and without (n=76) in-feed supplementation with a *Bacillus*-based DFM were collected and manure characteristics assessed. Quantities of methanogens and sulfate-reducing bacteria relative to total prokaryotes counts were determined by qPCR. The *Bacillus*-based DFM used in this example was the same as in Example 14. Manure samples were obtained and classified as in Example 14. Data was normalized for a manure height of 3.75 ft for statistical analysis.

The addition of the *Bacillus*-based DFM was associated with stabilization of the physical characteristics of the pit as can be seen by the numerical increase in pH as foaming severity increased across untreated pits while the pH of treated pits was constant regardless of the degree of foaming (Table 19). This stabilization is further evidenced by the numerical decrease in viscosity of untreated samples as degree of foaming increases compared to the viscosity of treated pits which were nearly constant across all degrees of foam. Additionally, administration of the *Bacillus*-based DFM lowered (P<0.05) the percentage of dry matter and the viscosity compared to untreated swine manure pits.

Sulfate-reducing bacteria are likely a larger portion of the population when there has been a disruption in anaerobic decomposition. The administration of the *Bacillus*-based DFM was associated with a reduction (P<0.05) in the quantity of sulfate-reducing bacteria compared to total prokaryotes suggesting that the anaerobic fermentation occurring in treated swine manure pits is more stable (Table 20). The quantity of methanogens compared to total prokaryotes increased (P<0.05) as the degree of foaming increased which was expected as methane gas is likely the gas being trapped by the foam in foaming swine manure pits. The quantity of methanogens compared to the total prokaryotes present in the swine manure pit increased (P<0.05) in pits administered the *Bacillus*-based DFM; however, there was less of an increase in methanogens as degree of foam increased, a fold change of 1.3, in the treated pits then there was in the untreated pits, which had a fold change of 2.0. This more stable methanogen population suggests that there was a more consistent anaerobic fermentation in the pits treated with a *Bacillus*-based DFM.

TABLE 19

Effect of probiotic *Bacillus* treatment and pit foaming category on physical manure characteristics.

| Probiotic | untreated pits | | | treated pits | | | Significance | | | |
|---|---|---|---|---|---|---|---|---|---|---|
| Fcat[1] | 0 | 1 | 2 | 0 | 1 | 2 | Probiotic | Fcat | P × F int. | SEM |
| DM | 9.451 | 8.322 | 7.861 | 6.682 | 6.598 | 5.957 | 0.002 | 0.379 | 0.221 | 0.157 |
| pH | 7.65 | 7.83 | 7.88 | 7.80 | 7.76 | 7.80 | 0.196 | 0.059 | 0.000 | 0.01 |
| Visc | 477.7 | 372.0 | 360.4 | 199.7 | 225.0 | 200.6 | 0.000 | 0.423 | 0.044 | 13.5 |

[1]Foaming categories: 0 = no to little foam (0-2 inches), 1 = moderate foam (3-15 inches), 2 = heavily foaming pit (>15 inches of foam)
Comments: Analysis normalized to 3.75 ft manure height, significance level α = 0.05.
DM = dry matter (in %), Visc = viscosity (in cps), Probiotic = probiotic *Bacillus* treatment, Fcat = foaming category, P × F int. = probiotic *Bacillus* treatment and foaming category interaction.

TABLE 20

Effect of probiotic *Bacillus* treatment and foaming category on methanogen and sulfate-reducing bacteria in swine manure pits.

| Probiotic | untreated pits | | | treated pits | | | Significance | | | |
|---|---|---|---|---|---|---|---|---|---|---|
| Fcat[1] | 0 | 1 | 2 | 0 | 1 | 2 | Probiotic | Fcat | P × F int. | SEM |
| MA | 0.0035 | 0.0059 | 0.0069 | 0.0064 | 0.0077 | 0.0084 | 0.001 | 0.013 | 0.919 | 0.0006 |
| SRB | 0.0383 | 0.0358 | 0.0262 | 0.0121 | 0.0141 | 0.0076 | 0.002 | 0.735 | 0.849 | 0.0023 |

[1]Foaming categories: 0 = no to little foam (0-2 inches), 1 = moderate foam (3-15 inches), 2 = heavily foaming pit (>15 inches of foam)
Comments: Analysis normalized to 3.75 ft manure height, significance level α = 0.05.
Probiotic = probiotic treatment, Fcat = Foaming category, MA = methanogenic archea, SRB = sulfate reducing bacteria, P × F int. = probiotic *Bacillus* treatment and foaming category interaction.
Data displayed in fold changes relative to prokaryote quantity in sample.

Example 17

Differences in Nitrogen Distribution and Fiber Characteristics, Mineral Content and Volatile Fatty Acid Profiles Associated with Probiotic *Bacillus* Treatment and Degree of Pit Foaming Manure samples from deep pit storage systems on swine production sites with and without in-feed supplementation with a *Bacillus*-based DFM were collected and the nutrient and mineral distribution and characteristics of these samples were assessed. The *Bacillus*-based DFM used in this example was the same as in Example 14. Additionally, manure samples from treated and untreated pits were collected from deep pit storage systems with and without foam. Manure samples were obtained and classified as in Example 14. Data was normalized for manure height of 3.75 ft for statistical analysis.

The administration of the *Bacillus*-based DFM was associated with a decrease (P<0.05) in nitrogen free extract (Table 21). The nitrogen free extract is a calculated value representing the amount of starches and sugars present in the pit, which are easily fermentable by microbes. The addition of the *Bacillus*-based DFM was also associated with lower (P<0.05) amounts of acid detergent fiber and neutral detergent fiber. The decrease of these compounds is an indication of fewer nutrients available for anaerobic digestion. The enzymatic production of the *Bacillus*-based DFM likely helped to reduce the amount of the nutrients in the swine manure pits and could help to regulate the anaerobic fermentation occurring and thus limit foaming. Additionally, the administration of the *Bacillus*-based DFM was associated with an increase (P<0.05) of aqueous ammonium bound nitrogen. The increased level of aqueous ammonium bound nitrogen is a sign that less ammonia is being released into the atmosphere.

The supplementation to the *Bacillus*-based DFM was associated with an increased (P<0.05) concentration of sodium and iron in swine manure pits (Table 22). Conversely, the concentrations of copper and manganese were reduced (P<0.05) when the *Bacillus*-based DFM was administered. As the degree of foaming increased the concentrations of copper, iron, and manganese were all decreased (P<0.05). The decreased level of minerals in the swine manure could indicate that there was an increased concentration of these minerals in the foam from an inversion of the two layers that happens when there was a disruption in anaerobic fermentation.

As the degree of foaming increased there was a decrease (P<0.05) in the concentration of crude fat (Table 23). This is likely a sign of an abnormally active microbial community consisting of filamentous microorganisms degrading the fat at the surface and trapping the gasses produced from the anaerobic fermentation occurring near the bottom of the swine manure pits. This is further evidenced by a decrease (P<0.05) in concentration of total VFAs, which is caused by the reduction (P<0.05) of acetate and propionate, the two most abundant VFAs in the swine manure pits. The administration of the *Bacillus*-based DFM reduced (P<0.05) the concentration of crude fat in the swine manure pits. The enzymatic activity of the *Bacillus* strains could be responsible for lowering the concentration of fats in the swine manure pits and help create an environment for a more consistent anaerobic fermentation.

TABLE 21

Effect of probiotic *Bacillus* treatment and foaming category on nitrogen distribution and fiber characteristics of swine manure pits.

| Probiotic | untreated pits | | | treated pits | | | Significance | | | |
|---|---|---|---|---|---|---|---|---|---|---|
| Fcat[1] | 0 | 1 | 2 | 0 | 1 | 2 | Probiotic | Fcat | P × F int. | SEM |
| NfE[2] | 9.086 | 6.310 | 5.625 | 2.621 | 3.028 | 2.538 | 0.001 | 0.505 | 0.144 | 0.671 |
| N | 6.629 | 8.322 | 7.447 | 7.557 | 9.620 | 8.686 | 0.535 | 0.091 | 0.978 | 0.539 |
| NH4_N | 5.707 | 5.767 | 6.021 | 8.344 | 8.007 | 8.669 | 0.000 | 0.492 | 0.752 | 0.158 |
| ADF_N | 0.539 | 0.535 | 0.652 | 0.772 | 0.745 | 0.730 | 0.242 | 0.996 | 0.823 | 0.039 |
| ADF | 17.131 | 17.979 | 18.891 | 16.032 | 15.705 | 15.599 | 0.000 | 0.264 | 0.169 | 0.236 |
| NDF | 40.857 | 40.292 | 36.912 | 33.911 | 33.498 | 33.495 | 0.017 | 0.996 | 0.582 | 0.684 |
| CF | 11.858 | 12.727 | 13.482 | 11.463 | 11.197 | 10.883 | 0.256 | 0.186 | 0.251 | 0.218 |

[1]Foaming categories: 0 = no to little foam (0-2 inches), 1 = moderate foam (3-15 inches), 2 = heavily foaming pit (>15 inches of foam)
[2]Calculated value, NfE = 100 − (crude protein + ether extract + crude fiber + ash), fraction contains mostly starches and sugars.
Comments: Analysis normalized to 3.75 ft manure height, significance level α = 0.05.
Probiotic = probiotic *Bacillus* treatment, Fcat = foaming category, NE = nitrogen free extract, N = nitrogen, NH4_N = aqueous ammonia bound nitrogen, ADF_N = acid detergent fiber bound nitrogen, ADF = acid detergent fiber, NDF = neutral detergent fiber, CF = crude fiber, P × F int. = probiotic *Bacillus* treatment and foaming category interaction.
All data in percent of total sample.

TABLE 22

Effect of probiotic Bacillus treatment and foaming category on mineral content of swine manure pits.

| Probiotic | untreated pits | | | treated pits | | | Significance | | | |
|---|---|---|---|---|---|---|---|---|---|---|
| Fcat 1 | 0 | 1 | 2 | 0 | 1 | 2 | Probiotic | Fcat | P × F int. | SEM |
| Ash | 19.463 | 20.848 | 20.706 | 22.188 | 21.652 | 20.891 | 0.823 | 0.319 | 0.217 | 0.275 |
| Ca | 2.103 | 2.125 | 1.906 | 2.083 | 2.040 | 1.755 | 0.581 | 0.602 | 0.882 | 0.042 |
| K | 3.841 | 4.472 | 4.669 | 4.910 | 4.944 | 5.228 | 0.753 | 0.375 | 0.248 | 0.088 |
| Mg | 1.230 | 1.290 | 1.195 | 1.395 | 1.278 | 1.253 | 0.360 | 0.336 | 0.199 | 0.021 |
| Na | 0.918 | 1.045 | 1.124 | 1.361 | 1.371 | 1.350 | 0.021 | 0.186 | 0.265 | 0.026 |
| P | 1.865 | 2.001 | 1.871 | 2.276 | 2.022 | 2.023 | 0.516 | 0.123 | 0.062 | 0.036 |
| S | 0.903 | 1.025 | 1.043 | 1.126 | 1.140 | 1.128 | 0.117 | 0.206 | 0.210 | 0.016 |
| Al | 0.513 | 0.703 | 0.523 | 0.514 | 0.505 | 0.415 | 0.316 | 0.386 | 0.511 | 0.036 |
| Cu | 0.381 | 0.442 | 0.359 | 0.384 | 0.351 | 0.324 | 0.001 | 0.009 | 0.109 | 0.010 |

TABLE 22-continued

Effect of probiotic Bacillus treatment and foaming category on mineral content of swine manure pits.

| Probiotic | untreated pits | | | treated pits | | | Significance | | | |
|---|---|---|---|---|---|---|---|---|---|---|
| Fcat [1] | 0 | 1 | 2 | 0 | 1 | 2 | Probiotic | Fcat | P × F int. | SEM |
| Fe | 1.605 | 1.629 | 1.494 | 2.295 | 2.211 | 1.850 | 0.001 | 0.009 | 0.109 | 0.049 |
| Mn | 0.359 | 0.378 | 0.354 | 0.377 | 0.368 | 0.342 | 0.004 | 0.005 | 0.509 | 0.006 |
| Zn | 1.286 | 1.275 | 0.998 | 1.857 | 1.807 | 1.383 | 0.358 | 0.195 | 0.598 | 0.059 |

[1]Foaming categories: 0 = no to little foam (0-2 inches), 1 = moderate foam (3-15 inches), 2 = heavily foaming pit (>15 inches of foam)
Comments: Analysis normalized to 3.75 ft manure height, significance level α = 0.05.
Probiotic = probiotic treatment, Fcat = Foaming category, P × F int. = probiotic *Bacillus* treatment and foaming category interaction.
All data in percent of total sample.

TABLE 23

Effect of probiotic Bacillus treatment and foaming category on fat and volatile fatty acid content of swine manure pits.

| Probiotic | untreated pits | | | treated pits | | | Significance | | | |
|---|---|---|---|---|---|---|---|---|---|---|
| Fcat[1] | 0 | 1 | 2 | 0 | 1 | 2 | Probiotic | Fcat | P × F int. | SEM |
| EE | 14.567 | 10.690 | 9.481 | 10.523 | 10.103 | 8.648 | 0.022 | 0.019 | 0.880 | 0.324 |
| Tot vFA[2] | 0.7388 | 0.4119 | 0.3886 | 0.5571 | 0.3680 | 0.2177 | 0.868 | 0.001 | 0.443 | 0.0283 |
| Acet | 0.4845 | 0.2844 | 0.2752 | 0.3718 | 0.2476 | 0.1894 | 0.588 | 0.003 | 0.597 | 0.0187 |
| Prop | 0.2175 | 0.1190 | 0.1038 | 0.1544 | 0.0954 | 0.0344 | 0.478 | 0.004 | 0.565 | 0.0101 |
| iButy | 0.0000 | 0.0000 | 0.0000 | 0.0000 | 0.0024 | 0.0000 | 0.069 | 0.414 | 0.485 | 0.0005 |
| Buty | 0.0051 | 0.0000 | 0.0000 | 0.0027 | 0.0000 | 0.0000 | 0.501 | 0.091 | 0.818 | 0.0008 |
| iVale | 0.0318 | 0.0084 | 0.0096 | 0.0282 | 0.0225 | 0.0024 | 0.501 | 0.221 | 0.469 | 0.0037 |

[1]Foaming categories: 0 = no to little foam (0-2 inches), 1 = moderate foam (3-15 inches), 2 = heavily foaming pit (>15 inches of foam)
[2]Value calculated as sum of vFAs. Valearate analysed but below vFA detection level.
Comments: Analysis normalized to 3.75 ft manure height, significance level α = 0.05.
Probiotic = probiotic *Bacillus* treatment, Fcat = Foaming category, EE = crude fat or ether extract, Tot vFA = total volatile fatty acids, Acet = acetate, Prop = propionate, iButy = iso-butyrate, Buty = butyrate, iVale = iso-valerate, P × F int. = probiotic *Bacillus* treatment and foaming category interaction.
All data in percent of total sample.

Example 18

*Bacillus* DFM Treatment Related Changes in Pit Bacterial Community

Manure samples from 217 randomly selected deep pit storage systems on swine production sites with (n=141) and without (n=76) in-feed supplementation with a *Bacillus*-based DFM were collected. The *Bacillus*-based DFM used in this example was the same as in Example 14. Manure samples were obtained and classified as in Example 14. Data was normalized for a manure height of 3.75 ft for statistical analysis.

Samples were combined with 10 mL of sterile tryptic soy broth (TSB)+10% glycerol broth and frozen at −20° C. until subsequent DNA isolation. Frozen samples were thawed on ice prior to DNA isolation. Solutions were vortexed for 30 seconds to yield a heterogeneous sample. Genomic DNA was extracted from one mL of each pit sample using a traditional phenol-chloroform isolation procedure. The resulting genomic DNA was further purified using the High Pure PCR Template Preparation Kit (Roche Applied Sciences).

Amplification reactions were performed as in Example 4. Generation of terminal restriction fragments (TRFs) and size analysis of TRFs were performed as in Example 4. Sample terminal-restriction fragment length polymorphism (T-RFLP) data from each individual site was analyzed as in Example 4.

Peak area was analyzed in a 2×3 factorial ANOVA using multivariate general linear model function of SPSS17.0 statistical software. Factors were probiotic *Bacillus* DFM treatment (no, yes) and foaming category (0=0-2 inches of foam, 1=3-15 inches of foam, 2=more than 15 inches of foam). Data was corrected for 3.75 ft manure height for statistical analysis.

Manure pit treatment with *Bacillus* DFM inhibited the growth of species related to TRFs bstu:61.29, bstu:224.09, hae:254.09, bstu:409.82, hae:296.66, hae:495.98 and hae:661.23 (P≤0.04) and supported bacterial species related to TRFs bstu:26.59, bstu:245.77, bstu:512.25, msp:77.01, msp:134.59 and msp:692.20 (P≤0.04; see Table 24). Bacterial species related to TRFs bstu:26.59, msp:77.01 and msp:692.20 were only detected in *Bacillus* DFM treated pits. Species bstu:245.77, bstu:512.25 and msp:204.70 were detected in higher quantities (P≤0.03) in *Bacillus* DFM treated pits, even though treated pits have proven to result in lower foam production (see Example 15). This indicates that these species did not promote foam production due to their higher abundance and might be called foam neutral species.

The effect of *Bacillus* DFM treatment was also determined as community stabilizing effect depending on foam category. All following statements refer to increased, decreased or steady bacterial quantity connected with changes from non-foaming (foam categories 0=0-2 inches of foam) to heavily foaming pits (foam category 2=more than 15 inches of foam). All fold changes stated were calculated based on significant changes (P≤0.05) in TRF quantities. The findings of this study indicated that *Bacillus* DFM treatment stabilized TRFs hae:31.05 (20.2 fold increase in untreated pits), hae:300.95 (12.5 fold increase in untreated) and hae:339.51 (9.4 fold increase in untreated) compared with minimal changes of quantity in treated pits and increasing foam category (Table 25). Bacterial species under proportionally increased in *Bacillus* DFM treated manure pits compared with untreated manure pits for TRFs bstu:95.51 (5.7 fold increase in untreated pits vs. 1.4 fold increase in treated pits), hae:299.93 (8.0 vs. 1.4 fold increase in treated), hae:321.99 (11.6 vs. 1.5 fold increase in treated), hae.:414.25 (24.7 vs. 1.2 fold increase in treated) and msp:485.92 (2.7 vs. 2.0 fold increase in treated). Bacterial species did under proportionally decrease in *Bacillus* DFM treated manure pits compared with untreated pits for TRFs bstu:193.30 (3.4 vs. 2.6 fold decrease in treated), msp:30.12 (20.7 vs. 13.9 fold decrease in treated), msp:206.88 (24.6 vs. 5.3 fold decrease in treated) and msp: 442.38 (8.5 vs. 1.7 fold decrease in treated).

Less severe changes with a reversed tendency due to higher foam category was observed for TRFs hae:216.49 (22.7 fold increase vs. 1.9 fold decrease in treated pits), hae:344.88 (121.3 fold increase vs. 2.9 fold decrease in treated), hae: 383.01 (54.8 fold increase vs. 2.4 fold decrease in treated), hae:409.86 (16.0 fold increase vs. 1.3 fold decrease in treated), hae:419.09 (>100.0 fold increase vs. 4.3 fold decrease in treated), hae:437.90 (57.7 fold increase vs. 1.7 fold decrease in treated), hae:473.37 (>100.0 fold increase vs. 2.0 fold decrease in treated) and msp:227.46 (2.8 fold decrease vs. 1.3 fold increase in treated).

Specific TRF related bacterial species have been identified which were not affected by *Bacillus* treatment but decreased or increased with foaming category. Bacterial species related to TRFs bstu:108:54, bstu:395.15, bstu:398.10, hae:63.20 and hae:287.91 increased 2 and 6 fold ($P \leq 0.04$) between foam categories 0 and 2 (Table 26). DFM treatment could aim at reducing the overgrowth of these species to prevent disruption of a stable and not foam causing bacterial community in swine manure pits. On the other hand, bacterial species related to TRFs bstu:535.76, bstu:558.95, hae:664.59, hae: 777.41, msp:57.16, msp:402.96 and msp:387.80 decreased between 5 and more than 100 fold ($P \leq 0.03$) between foam categories 0 and 2.

TABLE 24

Bacillus DFM treatment related changes in TRF associated bacteria unaffected by foam category in swine manure pits.

| TRF | untreated pits | | | treated pits | | | Significance | | | | |
|---|---|---|---|---|---|---|---|---|---|---|---|
| Fcat[1] -> | 0 | 1 | 2 | 0 | 1 | 2 | Probiotic | Fcat | P × F | SEM | Putative identification |
| bstu:61.29 | 518.42 | 526.13 | 705.55 | 396.30 | 365.72 | 342.00 | 0.041 | 0.895 | 0.179 | 61.89 | multiple species possible |
| bstu:224.09 | 2589.71 | 2357.64 | 3092.15 | 1611.70 | 1885.68 | 3110.78 | 0.033 | 0.920 | 0.712 | 202.67 | multiple species possible |
| bstu:291.02 | 2576.50 | 2279.97 | 1527.11 | 1295.38 | 1165.08 | 9.05 | 0.023 | 0.438 | 0.907 | 185.82 | *Chloroflexi* |
| bstu:512.25 | 1036.28 | 805.76 | 722.06 | 1869.98 | 1382.84 | 1449.01 | 0.034 | 0.657 | 0.945 | 147.01 | *Mycoplasma* |
| hae:254.09 | 896.27 | 1257/0 | 1055.92 | 398.31 | 412.82 | 580.26 | <.001 | 0.361 | 0.225 | 53.47 | *Chloroflexi* |
| hae:495.98 | 115.59 | 101.99 | 105.78 | 47.07 | 16.49 | 19.36 | <.001 | 0.448 | 0.928 | 10.77 | *Methylophilaceae* |
| hae:661.23 | 81.77 | 153.36 | 40.21 | 7.45 | 0.00 | 0.00 | 0.005 | 0.281 | 0.174 | 11.96 | not available |
| msp:77.01 | 0.00 | 0.00 | 0.00 | 10.54 | 6.20 | 31.50 | 0.009 | 0.260 | 0.187 | 2.38 | *Spomlactobacillus/Enterococcus* |
| msp:134.59 | 0.00 | 4.91 | 28.79 | 55.91 | 53.82 | 105.79 | 0.004 | 0.218 | 0.903 | 9.67 | multiple species possible |
| msp:204.70 | 376.08 | 384.21 | 342.34 | 654.88 | 897.35 | 1425.63 | 0.001 | 0.230 | 0.370 | 89.41 | *Chloroflexi* |
| msp:692.20 | 0.00 | 0.00 | 0.00 | 6.59 | 1.57 | 31.71 | 0.043 | 0.194 | 0.520 | 2.18 | not available |

[1]foaming categories: 0 = up to 2 inches of foam, 1 = between 2 and 15 inches of foam, 2 = more than 15 inches of foam.

Comments: Significance level α = 0.05; DFM = direct-fed microbial, TRF = terminal restriction fragment, Fcat = foaming category, Probiotic = *Bacillus* DFM treatment, P × F = *Bacillus* DFM treatment and foaming category interaction, SEM = standard error of the mean.

TABLE 25

Stabilizing effect on bacterial manure pit community related to Bacillus DFM treatment.

| TRF | untreated pits | | | treated pits | | | Significance | | | | |
|---|---|---|---|---|---|---|---|---|---|---|---|
| Fcat[1] -> | 0 | 1 | 2 | 0 | 1 | 2 | Probiotic | Fcat | P × F | SEM | Putative identification |
| bstu:95.51 | 1315.59 | 2548.21 | 7479.63 | 4082.46 | 3487.50 | 5912.05 | 0.938 | 0.007 | 0.071 | 309.50 | multiple species possible |
| bstu:193.30 | 4918.61 | 3469.64 | 1432.49 | 1877.54 | 1256.48 | 726.56 | <.001 | 0.007 | 0.053 | 167.91 | not available |
| hae:31.05 | 513.49 | 3881.00 | 10351.24 | 5039.84 | 3752.79 | 4466.79 | 0.001 | 0.971 | <.001 | 463.22 | not available |
| hae:216.49 | 148.53 | 3006.25 | 3374.79 | 1133.95 | 743.62 | 603.34 | <.001 | 0.073 | 0.001 | 206.08 | not available |
| hae:299.93 | 511.48 | 3265.38 | 4114.30 | 1999.45 | 1725.63 | 2960.00 | 0.048 | 0.338 | 0.050 | 276.87 | not available |
| hae:300.95 | 2285.91 | 3811.05 | 5826.32 | 2324.97 | 1778.46 | 2455.60 | <.001 | 0.561 | 0.050 | 197.17 | *Bacillus* |
| hae:321.99 | 270.86 | 1876.04 | 3141.25 | 1391.42 | 1404.14 | 2055.43 | 0.012 | 0.357 | 0.041 | 170.59 | *Enterococcus* |
| hae:339.51 | 58.30 | 179.53 | 546.35 | 243.44 | 211.87 | 268.71 | 0.039 | 0.417 | 0.008 | 24.57 | not available |
| hae:344.88 | 4.97 | 256.89 | 602.90 | 263.11 | 190.88 | 89.83 | <.001 | 0.412 | 0.001 | 34.88 | not available |
| hae:383.01 | 12.63 | 221.89 | 692.04 | 240.88 | 136.05 | 96.43 | <.001 | 0.780 | <.001 | 29.62 | *Desufotomaculum* |
| hae:409.86 | 60.83 | 412.31 | 973.13 | 327.44 | 244.36 | 241.80 | <.001 | 0.431 | <.001 | 38.30 | not available |
| hae:414.25 | 23.16 | 230.82 | 569.71 | 201.21 | 122.50 | 241.33 | 0.001 | 0.462 | 0.002 | 26.24 | not available |
| hae:419.09 | 0.00 | 107.77 | 370.26 | 152.47 | 91.79 | 35.69 | <.001 | 0.810 | <.001 | 16.15 | uncultured SRB |
| hae:437.90 | 17.82 | 424.59 | 1028.70 | 243.18 | 142.84 | 139.24 | <.001 | 0.232 | <.001 | 44.64 | not available |
| hae:473.37 | 0.00 | 97.63 | 341.68 | 95.30 | 44.91 | 47.55 | <.001 | 0.200 | <.001 | 13.99 | not available |
| msp:30.12 | 979.25 | 295.02 | 47.31 | 397.10 | 254.53 | 28.58 | 0.130 | <.001 | 0.007 | 40.11 | not available |
| msp:206.88 | 381.38 | 59.55 | 15.48 | 159.51 | 119.66 | 30.02 | 0.081 | <.001 | 0.086 | 25.98 | not available |
| msp:227.46 | 7861.11 | 3057.39 | 2768.80 | 5184.54 | 5582.26 | 6907.96 | 0.003 | 0.026 | 0.001 | 343.62 | *Desufotomaculum* |
| msp:442.38 | 797.24 | 339.09 | 94.18 | 275.38 | 157.63 | 203.79 | 0.063 | 0.011 | 0.075 | 45.44 | *Helicobacter* |
| msp:485.92 | 157.56 | 218.91 | 431.87 | 364.28 | 383.69 | 719.70 | 0.005 | 0.009 | 0.719 | 27.99 | not available |

[1]foaming categories: 0 = up to 2 inches of foam, 1 = between 2 and 15 inches of foam, 2 = more than 15 inches of foam.

Comments: Significance level α = 0.05; DFM = direct-fed microbial, TRF = terminal restriction fragment, Fcat = foaming category, Probiotic = *Bacillus* DFM treatment, P × F = Bacillus DFM treatment and foaming category interaction, SEM = standard error of the mean, SRO = sulfate reducing bacterium.

TABLE 26

Bacterial species associated with TRFs affected by foaming category but not affected by Bacillus DFM treatment as potential target for future DFM development.

| TRF | untreated pits | | | treated pits | | | Significance | | | | |
|---|---|---|---|---|---|---|---|---|---|---|---|
| Fcat[1] -> | 0 | 1 | 2 | 0 | 1 | 2 | Probiotic | Fcat | P × F | SEM | Putative TRF identification |
| bstu:108.54 | 1800.67 | 1664.14 | 5029.18 | 1478.25 | 2595.57 | 7478.12 | 0.358 | 0.001 | 0.417 | 342.68 | Capnocytophaga |
| bstu:395.15 | 364.46 | 663.28 | 1250.76 | 898.94 | 634.26 | 2014.68 | 0.328 | 0.042 | 0.215 | 96.26 | Methylophilaceae/Campylobacter |
| bstu:398.10 | 334.69 | 436.78 | 1705.96 | 754.87 | 435.63 | 2433.20 | 0.760 | 0.002 | 0.403 | 116.29 | Arcobacter |
| bstu:535.76 | 855.48 | 521.46 | 159.03 | 514.03 | 533.66 | 48.43 | 0.435 | 0.020 | 0.365 | 52.34 | not available |
| bstu:558.95 | 876.55 | 472.03 | 9.56 | 312.68 | 256.98 | 4.04 | 0.195 | 0.031 | 0.365 | 47.19 | Helicobacter |
| hae:62.20 | 1092.78 | 2839.22 | 2283.18 | 1258.33 | 1549.50 | 2653.89 | 0.178 | 0.042 | 0.053 | 156.08 | not available |
| hae:287.91 | 282.19 | 605.54 | 924.13 | 460.12 | 438.92 | 1541.49 | 0.611 | 0.038 | 0.200 | 80.46 | Enterococcus |
| hae:664.59 | 306.32 | 103.26 | 0.00 | 116.59 | 44.12 | 0.00 | 0.184 | 0.003 | 0.148 | 17.43 | not available |
| hae:777.41 | 214.82 | 208.95 | 0.00 | 128.49 | 267.11 | 0.00 | 0.755 | 0.022 | 0.148 | 29.20 | Campylobacter/Acrobacter |
| msp:57.16 | 59.66 | 4.79 | 11.21 | 25.39 | 4.75 | 0.00 | 0.309 | 0.034 | 0.514 | 6.01 | not available |
| msp:402.96 | 432.41 | 326.57 | 0.00 | 182.74 | 284.46 | 0.00 | 0.266 | 0.010 | 0.316 | 31.69 | not available |
| msp:387.80 | 279.44 | 410.03 | 25.43 | 433.11 | 415.84 | 44.54 | 0.647 | 0.021 | 0.776 | 44.06 | not available |

[1] foaming categories: 0 = up to 2 inches of foam, 1 = between 2 and 15 inches of foam, 2 = more than 15 inches of foam.
Comments: Significancelevel α = 0.05; DFM = direct-fed microbial, TRF = terminal restriction fragment, Fcat = foaming category, Probiotic = Bacillus DFM treatment, P × F = Bacillus DFM treatment and foaming category interaction, SEM = standard error of the mean.

It is understood that the various preferred embodiments are shown and described above to illustrate different possible features of the invention and the varying ways in which these features may be combined. Apart from combining the different features of the above embodiments in varying ways, other modifications are also considered to be within the scope of the invention.

BIBLIOGRAPHY

Bernet, N. and F. Beline. 2009. Challenges and innovations on biological treatment of livestock effluents. Bioresource Technology 100:5431-5436.

Bitton, G. 1994. Bulking and foaming in activated sludge plants. In *Wastewater Microbiology*. John Wiley & Sons, Inc., New York: pp. 167-187.

Brumm, M. 2009. *Brumm Speaks Out* blog located at www.mnpork.com/forum/index.php accessed on Oct. 20, 2009.

Frigon, D., R. M. Guthrie, G. T. Bachman, J. Royer, B. Bailey, and L. Raskin. 2006. Long-term analysis of a full-scale activated sludge waterwater treatment system exhibiting seasonal biological foaming. Water Research 40:990-1008.

Fu, S. X., M. Johnston, R. W. Fent, D. C. Kendall, J. L. Usry, R. D. Boyd, and G. L. Allee. 2004. Effect of corn distiller's dried grains with soluble (DDGS) on growth, carcass characteristics and fecal volume in growing-finishing pigs. Journal of Animal Science 82 (Suppl. 2):80.

Gonzalez-Fernandez, C. and P. A. Garcia-Encina. 2009. Impact of substrate to inoculum ratio in anaerobic digestion of swine slurry. Biomass and Bioenergy 33:1065-1069.

Hoff, S. J., D. S. Bundy, M. A. Nelson, B. C. Zelle, L. D. Jacobson, A. J. Heber, N. I. Jiqin; Y. Zhang, J. A. Koziel, and D. B. Beasley. 2006. Emissions of ammonia, hydrogen sulfide, and odor before, during, and after slurry removal from a deep-pit swine finisher. Journal of the Air & Waste Management Association 56:581-590.

Lemmer, H. 1986. The ecology of scum causing *Actinomycetes* in sewage treatment plants. Water Research 20:531-535.

Lemmer, H. and M. Baumann. 1988. Scum *Actinomycetes* in sewage treatment plants: part 2 The effect of hydrophobic substrate. Water Research 22:761-763.

NRC, 1998. National Research Council Nutrient Requirements of Swine, 10$^{th}$ Revised Edition. National Academy Press, Washington, D.C.

Pagilla, K., K. Craney, and W. Kido. 1997. Causes and effects of foaming in anaerobic sludge digesters. Water Science Technology 36:463-470.

Pagilla, K. R., A. Sood, and H. Kim. 2002. *Gordonia (Nocoardia) amarae* foaming due to biosurfactant production. Water Science and Technology 46:519-524.

Peu, P., H. Brugere, A. Pourcher, M. Kerouredan, J. Godon, J. Delgenes, and P. Dabert. 2006. Dynamics of a pig slurry microbial community during anaerobic storage and management. Applied and Environmental Microbiology 72:3578-3585.

Pujol, R., P. Duchene, S. Schetrite, and J. P. Canler. 1991. Biological foams in activated sludge plants: characterization of the situation. Water Research 25:1399-1404.

Rehberger, J., E. Davis, A. Baker, T. Parrott, A. Veldkamp, and T. Rehberger. 2009. A preliminary comparison of bacterial communities of foaming and non-foaming swine manure pits. Journal of Animal Science 87(Suppl. 2):492.

Stein, H. H. and G. C. Shurson. 2009. BOARD INVITED REVIEW: The use and application of distillers dried grains with solubles in swine diets. Journal of Animal Science 87:1292-1303.

Shurson, J. 2009. Analysis of current feeding practices of distiller's grains with soluble in livestock and poultry feed relative to land use credits associated with determining the low carbon fuel standard for ethanol. Accessed at; www.ethanolrfa.org/objects/documents/2288/rfa.analysis_of_current_feeding_practices_of_distiller_final_3-25-09.pdf on Oct. 23, 2009.

Snell-Castro, R., J. Godon, J. Delgenes, and P. Dabert. 2005. Chracterization of the microbial diversity in a pig manure storage pit using small subunit rDNA sequence analysis. FEMS Microbiology Ecology 52:229-242.

Soddell, J. 1999. Foaming. In *The Microbiology of Activated Sludge*. eds. R. J. Seviour and L. L. Blackall. Academic Publishers, Dordrecht, the Netherlands: pp. 161-201.

Soddell, J. A. and R. J. Seviour. 1990. Microbiology of foaming in activated sludge plants. Journal of Applied Bacteriology 69:145-176.

Soddell, J. A. and R. J. Seviour. 1995. Relationship between temperature and growth of organisms causing *Nocardia* foams in activated sludge plants. Water Research 29:1555-1558.

Whitehead, T. R. and M. A. Cotta. 2001. Characterization and comparison of microbial populations in swine faeces and manure storage pits by 16S rDNA gene sequence analyses. Anaerobe 7:181-187.

Wolfe, R. S. 1971. Microbial formation of methane. Adv. Microbiol. Physiol. 6: 107-145.

Zhu, J. 2000. A review of microbiology in swine manure odor control. Agriculture, Ecosystems, and Environment 78: 93-106.

What is claimed is:

1. A method of controlling foam in a manure pit, the method comprising administering *Bacillus* strains in an effective amount to pigs whose manure is stored in the manure pit, the *Bacillus* strains comprising:
   - *B. licheniformis* 842 (NRRL B-50516) or a strain having all of the identifying characteristics of the *B. licheniformis* 842 (NRRL B-50516);
   - *B. subtilis* 27 (NRRL B-50105) or a strain having all of the identifying characteristics of the *B. subtilis* 27 (NRRL B-50105); and
   - *B. licheniformis* 21 (NRRL B-50134) or a strain having all of the identifying characteristics of the *B. licheniformis* 21 (NRRL B-50134), wherein
   70% of the total CFUs of the *Bacillus* strains is *B. licheniformis* 842 (NRRL B-50516) or a strain having all of the identifying characteristics of the *B. licheniformis* 842 (NRRL B-50516),
   10% of the total CFUs of the *Bacillus* strains is *B. subtilis* 27 (NRRL B-50105) or a strain having all of the identifying characteristics of the *B. subtilis* 27 (NRRL B-50105), and
   20% of the total CFUs of the *Bacillus* strains is *B. licheniformis* 21 (NRRL B-50134) or a strain having all of the identifying characteristics of the *B. licheniformis* 21 (NRRL B-50134), and
   wherein strains are administered at a rate of at least about $1.0 \times 10^5$ CFU per gram of feed fed to the pigs.

2. The method of claim 1, wherein administration of the *Bacillus* strains delays foam formation when compared to foam formation in a control manure pit not administered the *Bacillus* strains.

3. The method of claim 1, wherein the strains are administered at a rate of at least about $2.0 \times 10^8$ CFU per gram of feed fed to the pigs.

4. The method of claim 1, wherein the strains are administered at a rate of at least about $2.2 \times 10^8$ CFU per gram of feed fed to the pigs.

5. The method of claim 1, wherein the strains are administered at a rate of at least about $2.5 \times 10^8$ CFU per gram of feed fed to the pigs.

6. The method of claim 1, wherein the *Bacillus* strains further comprise *B. subtilis* LSSAO1 (NRRL B-50104) or a strain having all of the characteristics of the *B. subtilis* LSSAO1 (NRRL B-50104).

* * * * *